(12) United States Patent
Acker et al.

(10) Patent No.: US 12,310,602 B2
(45) Date of Patent: May 27, 2025

(54) MILLING APPARATUS FOR IMPLANTING A JOINT PROSTHESIS

(71) Applicant: Bioshift, LLC, Ketchum, ID (US)

(72) Inventors: Randall Lane Acker, Ketchum, ID (US); Gregory Thomas Van Der Meulen, Ketchum, ID (US)

(73) Assignee: BioShift, LLC, Ketchum, ID (US)

( * ) Notice: Subject to any disclaimer, the term of this patent is extended or adjusted under 35 U.S.C. 154(b) by 0 days.

(21) Appl. No.: 18/083,959

(22) Filed: Dec. 19, 2022

(65) Prior Publication Data

US 2023/0190312 A1    Jun. 22, 2023

Related U.S. Application Data

(60) Continuation of application No. 17/030,276, filed on Sep. 23, 2020, now Pat. No. 11,529,151, which is a division of application No. 15/711,899, filed on Sep. 21, 2017, now Pat. No. 10,799,253, which is a continuation of application No. 13/193,196, filed on
(Continued)

(51) Int. Cl.
| | |
|---|---|
| *A61B 17/17* | (2006.01) |
| *A61B 17/15* | (2006.01) |
| *A61F 2/38* | (2006.01) |
| *A61F 2/46* | (2006.01) |
| *A61F 2/30* | (2006.01) |

(52) U.S. Cl.
CPC .......... *A61B 17/1739* (2013.01); *A61B 17/15* (2013.01); *A61F 2/3804* (2013.01); *A61F 2/4605* (2013.01); *A61F 2002/307* (2013.01); *A61F 2/30767* (2013.01); *A61F 2002/3818* (2013.01); *A61F 2002/4687* (2013.01)

(58) Field of Classification Search
CPC ... A61B 17/17; A61B 17/171; A61B 17/1739; A61B 17/1764; A61B 17/1775
See application file for complete search history.

(56) References Cited

U.S. PATENT DOCUMENTS

| 3,852,831 A | 12/1974 | Dee |
| 4,293,963 A | 10/1981 | Gold et al. |
| (Continued) | | |

FOREIGN PATENT DOCUMENTS

| DE | 10061883 | 6/2002 |
| EP | 0132284 | 1/1985 |
| (Continued) | | |

OTHER PUBLICATIONS

Pagano, et al., "Unicompartmental Knee Arthroplasty," *The Knee*, Chapter 76, pp. 1002-1012.
(Continued)

*Primary Examiner* — Nicholas W Woodall
(74) *Attorney, Agent, or Firm* — Klarquist Sparkman, LLP

(57) ABSTRACT

A novel and improved elbow prosthesis and method of implanting same including a prosthesis system that has a retaining system. The joint prosthesis system can include an implant, and an alignment guide. The alignment guide can include a post member extending through a central axis of rotation in a prosthesis and a drill guide member having a first limiting member for limiting articular surface removal from a joint. The first limiting member can include a recessed guide for positioning the implant.

12 Claims, 23 Drawing Sheets

Related U.S. Application Data

Jul. 28, 2011, now Pat. No. 9,782,184, which is a division of application No. 12/011,337, filed on Jan. 25, 2008, now Pat. No. 8,012,214, which is a continuation-in-part of application No. 11/237,171, filed on Sep. 27, 2005, now Pat. No. 8,034,113.

(56) References Cited

U.S. PATENT DOCUMENTS

| | | | |
|---|---|---|---|
| 4,301,552 A | 11/1981 | London | |
| 4,378,607 A | 4/1983 | Wadsworth | |
| 4,399,813 A | 8/1983 | Barber | |
| 4,538,306 A | 9/1985 | Dorre et al. | |
| 4,624,250 A | 11/1986 | Saunders et al. | |
| 4,719,908 A | 1/1988 | Averill et al. | |
| 4,721,104 A * | 1/1988 | Kaufman | A61B 17/1764 606/88 |
| 4,822,364 A | 4/1989 | Inglis et al. | |
| 4,952,214 A | 8/1990 | Comparetto | |
| 5,030,237 A | 7/1991 | Sorbie et al. | |
| 5,147,364 A | 9/1992 | Comparetto | |
| 5,282,867 A | 2/1994 | Mikhail | |
| 5,376,121 A | 12/1994 | Huene et al. | |
| 5,413,607 A * | 5/1995 | Engelbrecht | A61F 2/385 623/20.24 |
| 5,578,038 A | 11/1996 | Slocum | |
| 5,634,927 A | 6/1997 | Houston et al. | |
| 5,782,923 A | 7/1998 | Engelbrecht et al. | |
| 5,840,078 A | 11/1998 | Yerys | |
| 5,879,395 A | 3/1999 | Tornier et al. | |
| 6,051,751 A | 4/2000 | Sioshansi et al. | |
| 6,066,142 A | 5/2000 | Serbousek et al. | |
| 6,132,468 A | 10/2000 | Mansmann | |
| 6,162,253 A | 12/2000 | Conzemius et al. | |
| 6,168,626 B1 | 1/2001 | Hyon et al. | |
| 6,190,390 B1 | 2/2001 | McAllister | |
| 6,217,615 B1 | 4/2001 | Sioshansi et al. | |
| 6,306,171 B1 | 10/2001 | Conzemius | |
| 6,409,768 B1 | 6/2002 | Tepic et al. | |
| 6,554,838 B2 | 4/2003 | McGovern et al. | |
| 6,652,586 B2 | 11/2003 | Hunter et al. | |
| 6,660,040 B2 | 12/2003 | Chan et al. | |
| 6,890,357 B2 | 5/2005 | Tornier | |
| 6,997,957 B2 | 2/2006 | Huene | |
| 7,083,623 B2 | 8/2006 | Michelson | |
| 7,150,761 B2 | 12/2006 | Justin et al. | |
| 7,182,766 B1 | 2/2007 | Mogul | |
| 7,247,170 B2 | 7/2007 | Graham et al. | |
| 7,942,882 B2 | 5/2011 | Tornier et al. | |
| 8,034,113 B2 | 10/2011 | Acker et al. | |
| 8,939,984 B2 | 1/2015 | Budoff | |
| 2004/0220675 A1 | 11/2004 | Lewis et al. | |
| 2005/0165487 A1 | 7/2005 | Muhanna et al. | |
| 2005/0192588 A1 | 9/2005 | Garcia | |
| 2006/0052791 A1 | 3/2006 | Hagen et al. | |
| 2007/0265634 A1 | 11/2007 | Weinstein et al. | |

FOREIGN PATENT DOCUMENTS

| | | |
|---|---|---|
| EP | 1142542 | 10/2001 |
| EP | 1864617 | 12/2007 |
| GB | 2094638 | 9/1982 |
| GB | 2334890 | 9/1999 |
| WO | WO 97/07753 | 3/1997 |

OTHER PUBLICATIONS

Trostel, et al., "Canine Elbow Displasia: Anatomy and Pathogenesis," *Compendium*, Oct. 2003, 25(10), pp. 754-761.

* cited by examiner

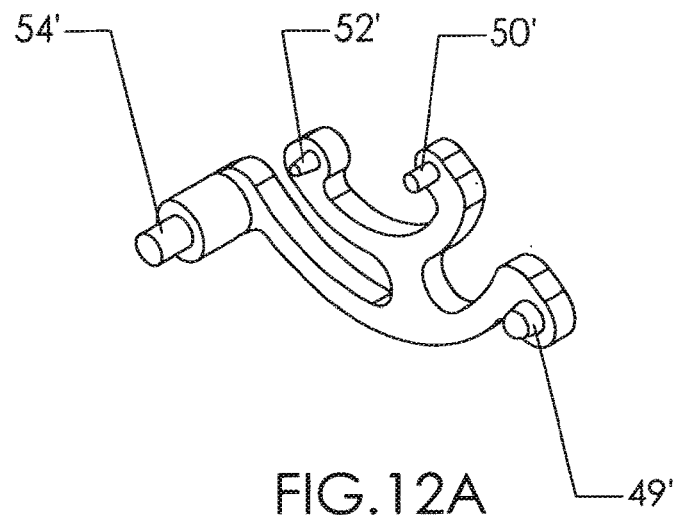
FIG.12A
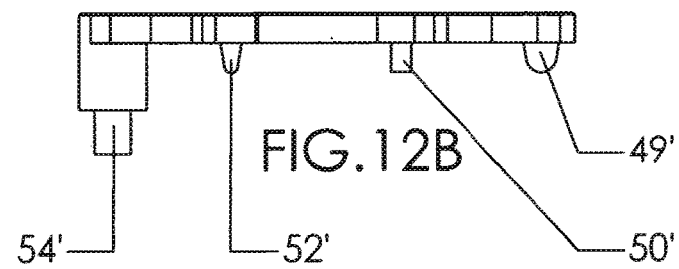
FIG.12B
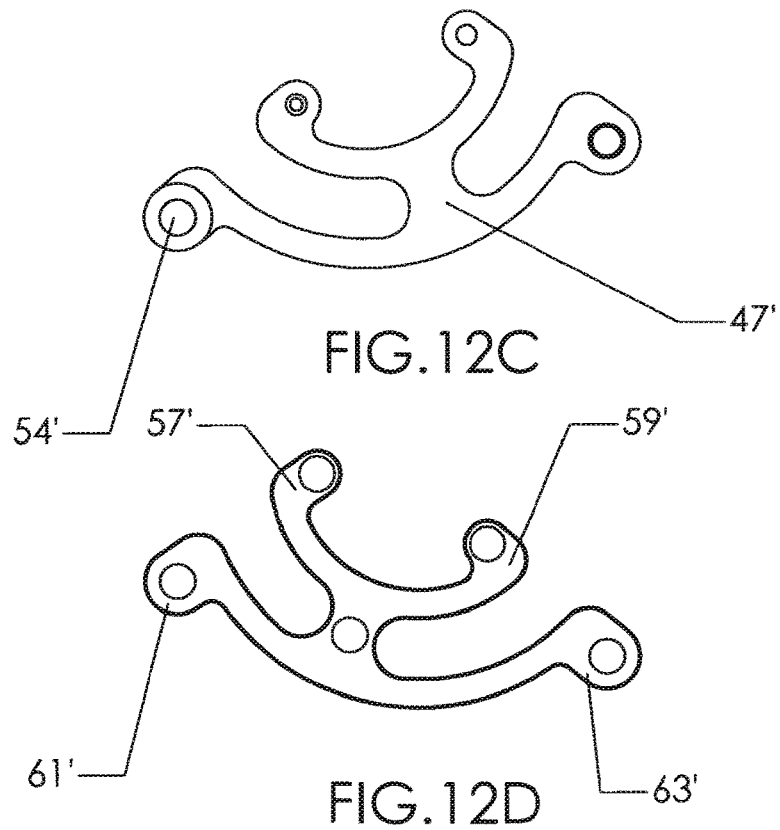
FIG.12C
FIG.12D

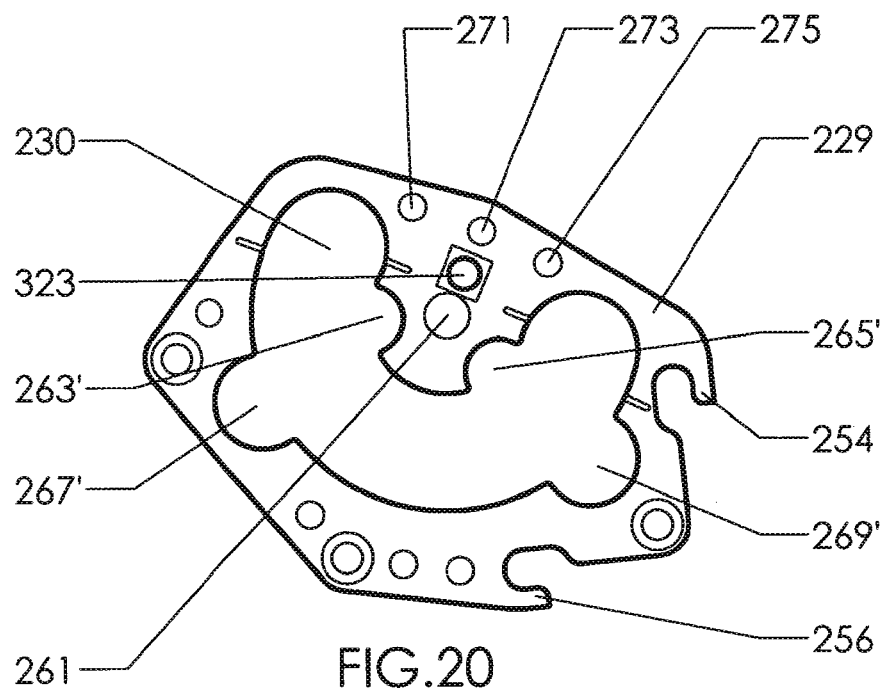
FIG.19
FIG.20
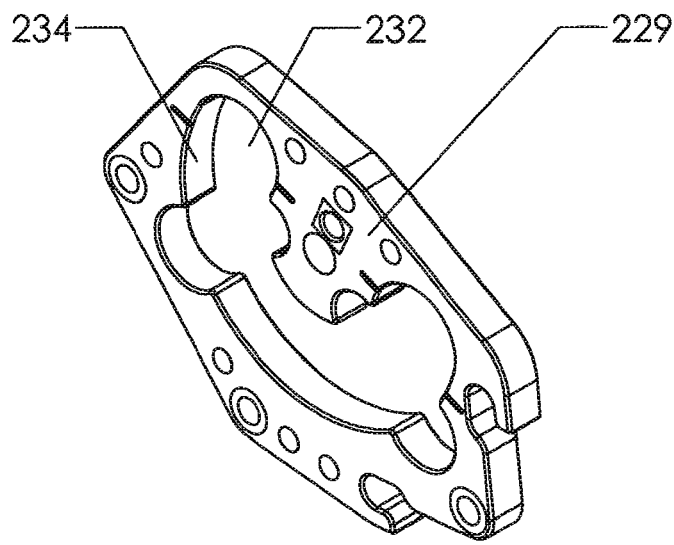
FIG.21

MILLING APPARATUS FOR IMPLANTING A JOINT PROSTHESIS

CROSS REFERENCE TO RELATED APPLICATION

This application is a continuation of U.S. patent application Ser. No. 17/030,276, filed Sep. 23, 2020, which is a divisional of U.S. patent application Ser. No. 15/711,899, filed Sep. 21, 2017, now U.S. Pat. No. 10,799,253, which is a continuation of U.S. application Ser. No. 13/193,196, filed Jul. 28, 2011, now U.S. Pat. No. 9,782,184, which is a divisional of U.S. application Ser. No. 12/011,337, filed Jan. 25, 2008, now U.S. Pat. No. 8,012,214, which is a continuation-in-part of U.S. patent application Ser. No. 11/237,171, filed Sep. 27, 2005, now U.S. Pat. No. 8,034,113; each of these applications is incorporated by referenced herein in its entirety.

BACKGROUND

The article of manufacture and method relate broadly to a joint prosthesis and method of implanting same, and more particularly to a mammalian joint prosthesis and novel and improved method of implanting same.

The majority of mammalian joints are hinge-type synovial joints formed where a distal end of a bone articulates with a proximal end of an opposite or complementary bone. Joint dysplasia is a common debilitating condition that affects mammals and more specifically the canine elbow joint. The current surgical techniques result in an unacceptable failure rate of the implant due to the technical difficulties associated with the implantation procedure as well as excessive post-surgical physical therapy needs as a result of the invasiveness of the procedure and the abundance of soft tissue damage.

There is therefore a need for a novel and improved joint arthroplasty that involves a minimally invasive surgical technique with a novel implant. The following embodiments and aspects thereof are described and illustrated in conjunction with systems, tools and methods which are meant to be exemplary and illustrative, not limiting in scope. In various embodiments, one or more of the above described problems have been reduced or eliminated, while further embodiments are directed to other improvements.

SUMMARY

The embodiments and methods set forth are exemplary and not for purposes of limitation. The present embodiments and methods are designed to provide a novel and improved elbow joint prosthesis and method of implanting same incorporating a first member having a first bone fixation surface and a first articulating surface, a complementary second member having a second bone fixation surface and a second articulating surface the second articulating surface portion having intersecting concave and convex surfaces defining alternate upwardly and downwardly curved projections as well as an opposite second bone fixation portion, the first and second bone fixation surfaces being disposed opposite to the first and second articulating surfaces, and a set plate member adapted to receive the first and second members.

The first and second members form an articulating prosthetic joint implant. The implant utilizes unique bone-stabilizing pegs as well as bone-receiving beads promoting bone ingrowth and reducing aseptic loosening. The anatomical duplication of the joint preserves flexion and extension while reducing excessive pulling of ligaments. A novel set plate member releasably links the first and second members and aids in positioning of the implant, forming an aggregate implant.

Methods are also provided for a novel and improved joint arthroplasty. One such method, offered by way of example but not limitation, of implanting an endoprosthesis comprises the steps of exposing a medial or lateral joint of a subject, implanting a pin member through a central axis of rotation of a joint, drilling prosthesis post cavities in the joint, milling articular surfaces and press-fitting the prosthesis. The medial approach in elbow joint arthroplasty, which is usually the area most affected by elbow dysplasia is proposed but other approaches such as lateral may be used as well. This will result in a lower failure rate of the implant due to superior biomechanics of the implant, a lower degree of invasion of the joint capsule and ligamentous structure while reducing periarticular scarring. Milling arthroplasty results in less structural damage to the joint, provides good trabecular structure to support the implant without subsidence, low infection rates and little bleeding. The current implant may be inserted without disarticulating the joint thereby enabling an earlier return to weight bearing and walking while providing for a minimally invasive technique. The implantation of all members of a total joint prosthesis with only one implantation step is novel and reduces trauma to the subject.

The foregoing examples of the related art and limitations related therewith are intended to be illustrative and not exclusive. Other limitations of the related art will become apparent to those skilled in the art upon a reading of the Specification and study of the Drawings. In addition to the exemplary aspects and embodiments described above, further aspects and embodiments will become apparent by reference to the Drawings and by study of the following Description.

BRIEF DESCRIPTION OF THE DRAWINGS

FIG. 12A-12D are multiple views of the set plate shown in FIG. 1;

FIG. 19 is a side view of the alignment plate of FIG. 17;

FIG. 20 is a bottom view of an alignment plate;

FIG. 21 is a perspective view of an alignment plate;

Exemplary embodiments are illustrated in referenced figures. of the drawings. It is intended by the embodiments and figures disclosed herein are to be considered illustrative rather than limiting.

DETAILED DESCRIPTION

Figure 1:
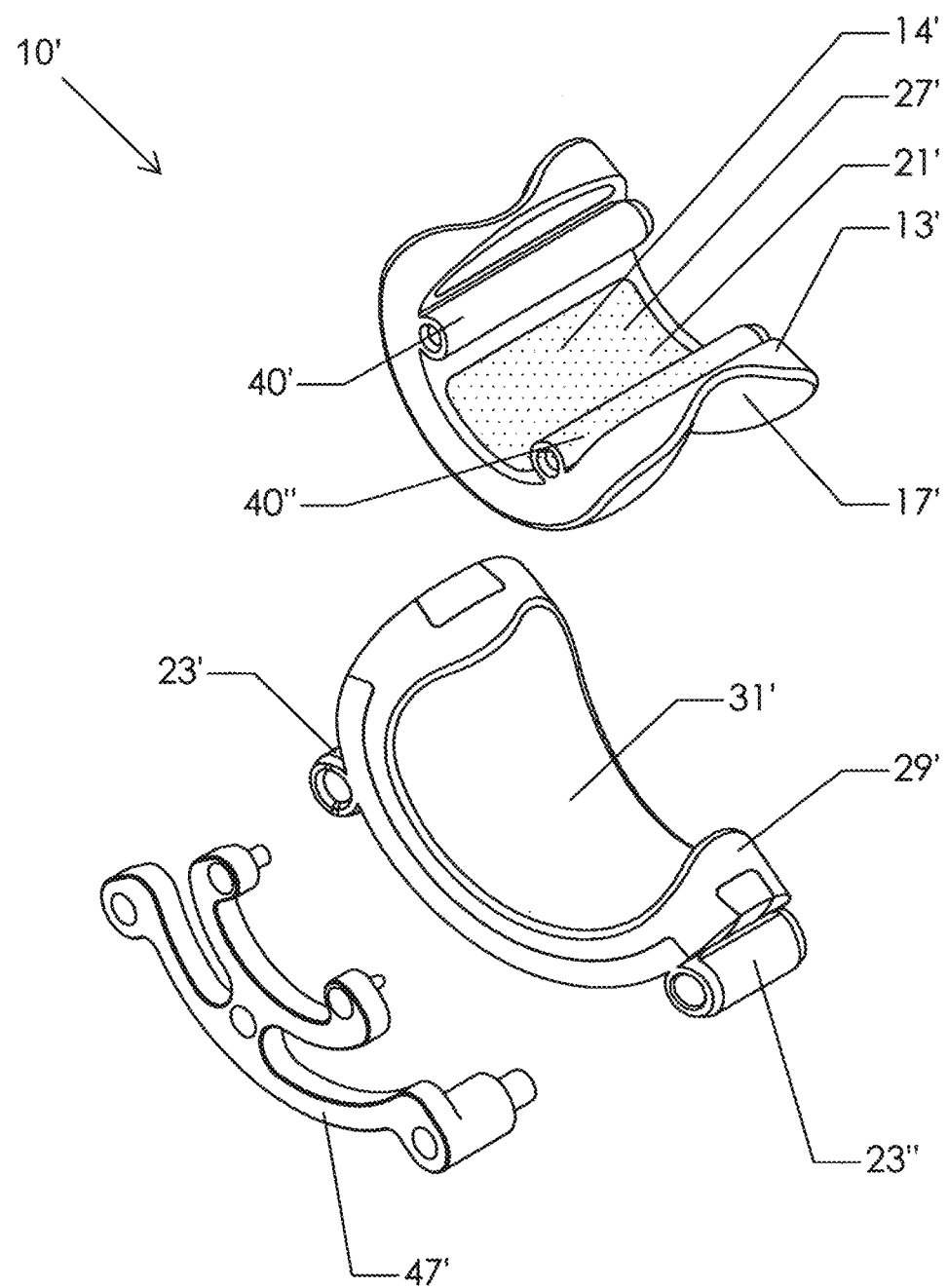
FIG. 1 is a perspective view of an embodiment of a joint prosthesis including a set plate.
Figure 3:
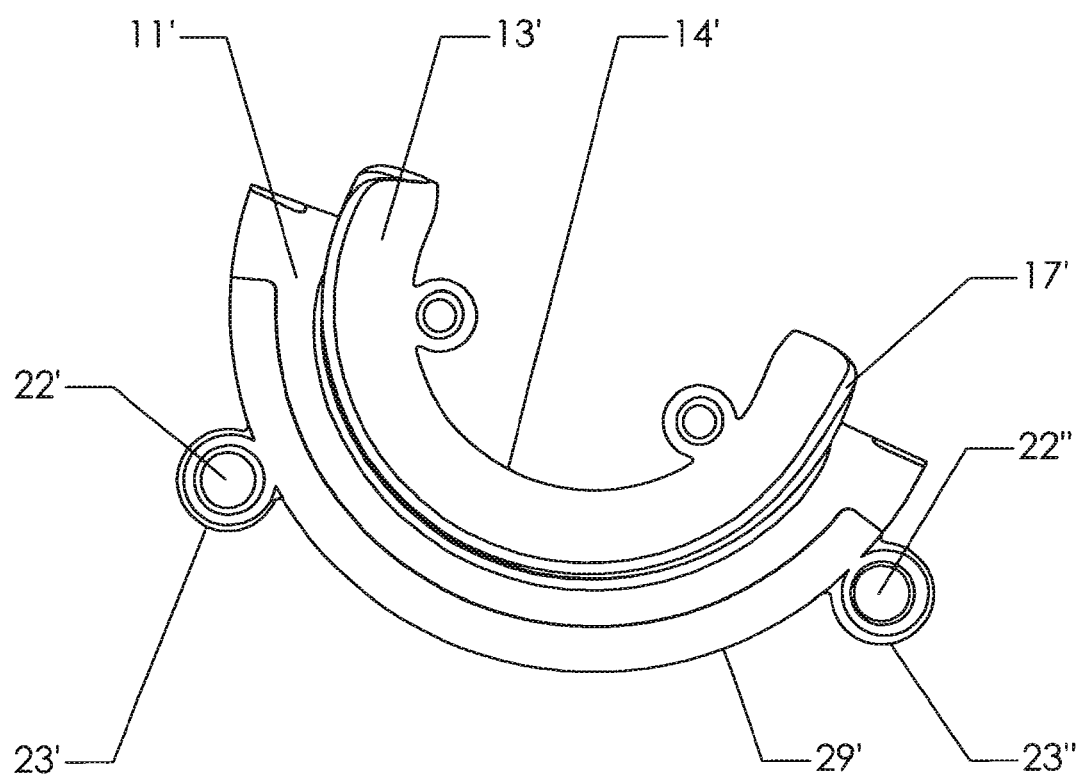
FIG. 3 is a side view of the implant of FIG. 1 without a set plate.
Figure 4:
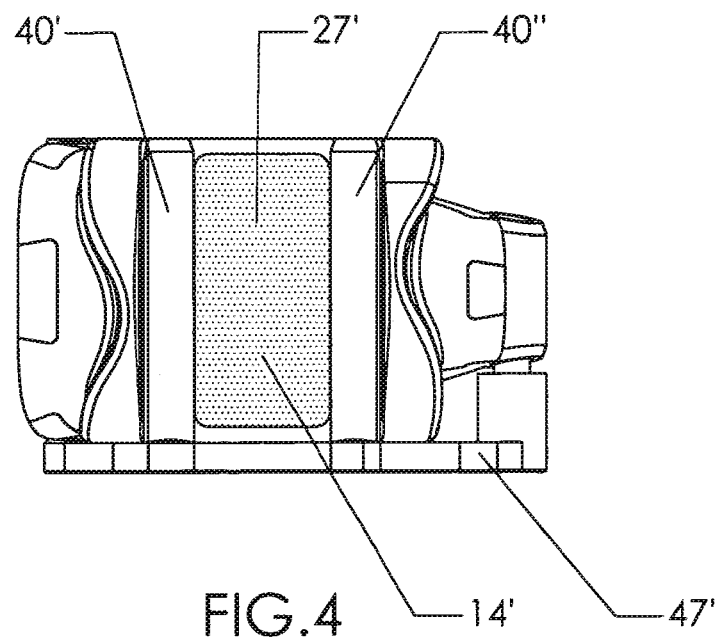
FIG. 4 is a top plan view of the implant as shown in FIG. 1.
Figure 9:
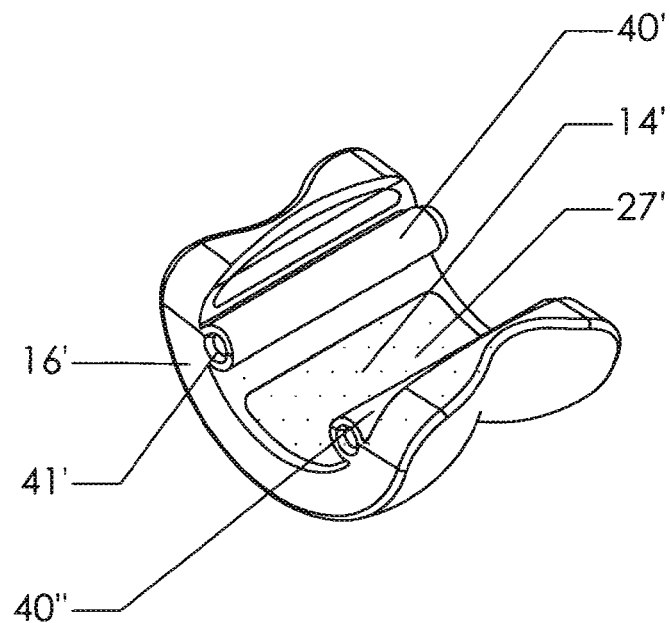
FIG. 9 is a perspective view of a humeral component.
Figure 10:
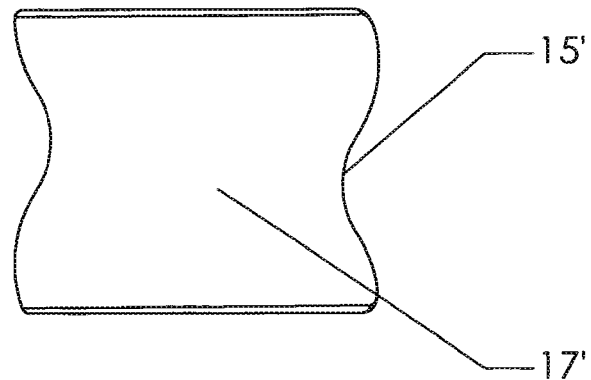
FIG. 10 is a bottom plan view of the humeral component of FIG. 9.

In the embodiments shown in FIGS. 1-14, there is provided an implant 11' with a humeral condylar component 13' and a radioulnar component 29'. The humeral component 13' includes a first articulating surface portion 17' of substantially saddle-shaped configuration, as shown in FIGS. 1, 9 and 10, and an opposite first bone fixation portion 14', as shown in FIGS. 1, 4 and 9. Geometrically, the saddle-shaped configuration of the first articulating surface portion 17' is broadly in the form of a concave configuration along planes parallel to its major axis and generally convex in planes transverse to the major axis, the degree of convexity lessening or flattening out, toward the center of the major axis. The humeral condylar component 13' is generally half-moon shaped, having an outer convex articulating surface 17' and inner concave surface, and made of cobalt-chrome molybdenum (Co-CrMb), titanium, Ti-alloy or ceramic but may also be made of other materials. The first articulating surface 17' as shown in FIG. 10 has a longitudinally extending angular groove 15' and simulates or approximates the natural shape of a trochlea humerus which on a canine for example, is a medially located, arcuate pulley-shaped member. The groove 15' extends diagonally across the surface and extends at an acute angle to an imaginary plane through a major axis of the first articulating surface portion 17'. The first bone fixation portion 14' of the humeral component 13' has a concave, semi-circular surface 21'. The concave surface 21' is complementary to the first articulating surface 17' and includes transversely extending cylindrical retaining members or protuberances 40', 40". The retaining members 40', 40" may be hollow or have shallow openings 41', 41" at one end with the open end extending up to outer peripheral edges 16' of the first bone fixation portion 14'. The openings 41', 41" are designed to receive a set plate 47' which will be discussed in more detail at a later point. The retaining members 40', 40" typically are evenly spaced from the ends and extend transversely to a major axis of the humeral component 13'. The retaining members 40', 40" may extend the width of the component 13' and in this embodiment do not extend beyond the outer peripheral edge 16' of the humeral component 13'. Alternatively, the retaining members 40', 40" could extend beyond the outer edges of the component or could end short of the outer edges of the component. The first bone fixation portion 14' may also include porous members, such as, PCA beads 27' which also promote bone growth. The PCA beads are manufactured by Bio-Vac, Inc., of Michigan, USA. Other possible fixation members include hydroxyl apatite (HA) coating, titanium plasma spray coating or Resorbably Blast Media Coating to name a few. Bony fixation of prosthetic implants is encouraged with surface extensions, such as, the retaining members 40', 40" which form a primary fixation for the implant. Beaded porous members provide secondary fixation allowing for bony ingrowth. A proximal portion 20' of the humeral component 13' which is the first bone fixation portion 14' contacts a distal surface 28' of the humerus 12' providing for an interference fit between the bone fixation portion and the humerus 12', as shown in FIG. 2

Figure 11:
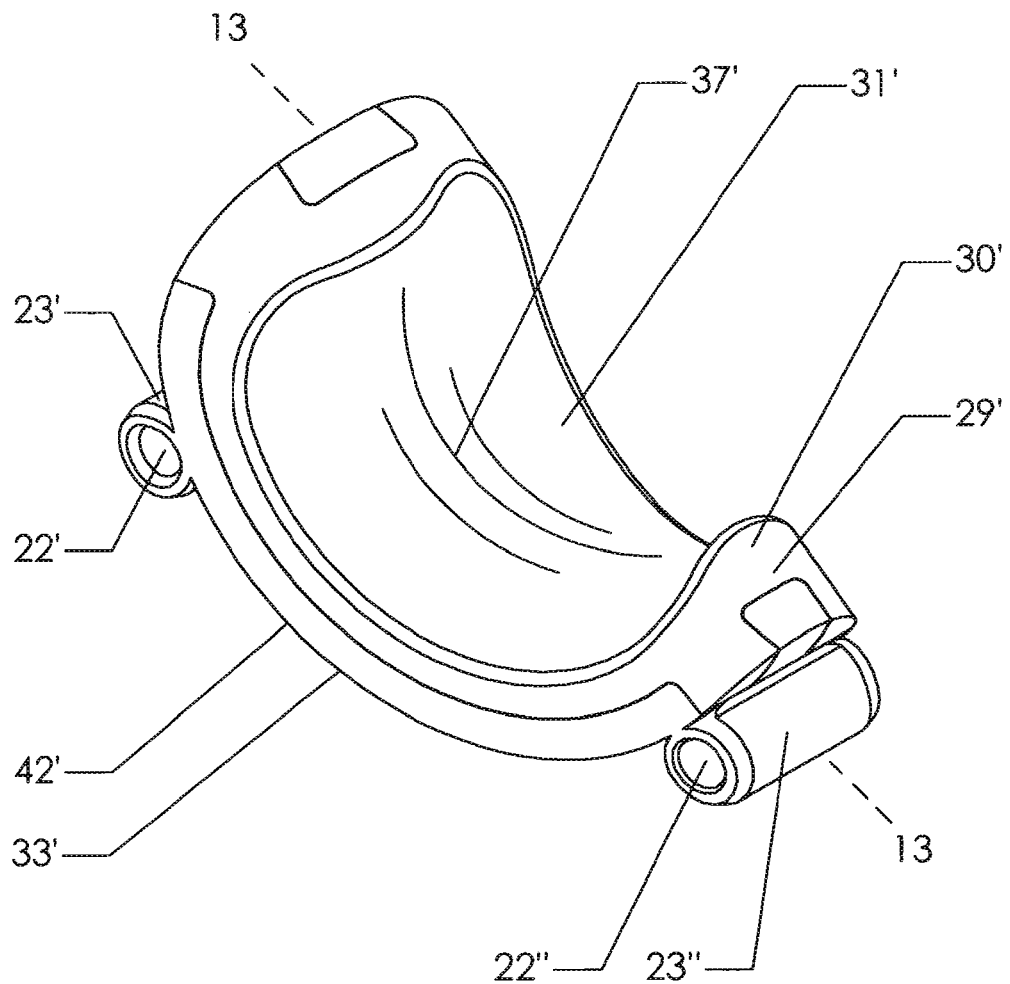
FIG. 11 is a perspective view of an ulnar component.

The radioulnar component 29' has opposing surfaces including a second articulating surface portion 31' and a second bone fixation portion 33'. The radioulnar component 29' is half-moon shaped and in the embodiment shown is slightly tapered at a posterior end 30'. Other forms of the component may also be used without a slightly tapered end as the component is designed to approximate the joint component of a particular species. The second articulating surface portion 31' has a saddle-shaped or concave configuration that faces cranially. The articulating surface portion 31' contains a medial ridge member 37' having intersecting convex and concave surfaces defining alternate upwardly and downwardly curved projections. The ridge member 37', in the embodiment shown, simulates a trochlear ridge but may also be designed to simulate the approximate anatomy of the joint such as an intercondylar eminence, articulating surface of the talus or trochlea of the human, and is complementary to the groove 15' of the first articulating surface portion of the corresponding component 13'. The ridge 37' as shown in FIG. 11, extends diagonally across the concave surface at a substantially mid-level portion between the concave and convex surfaces and extends at an acute angle to an imaginary line through a major axis of the second articulating surface portion 31'. The extension of the ridge 37' approximates the natural helical shape of a trochlear notch in a canine.

Figure 2:
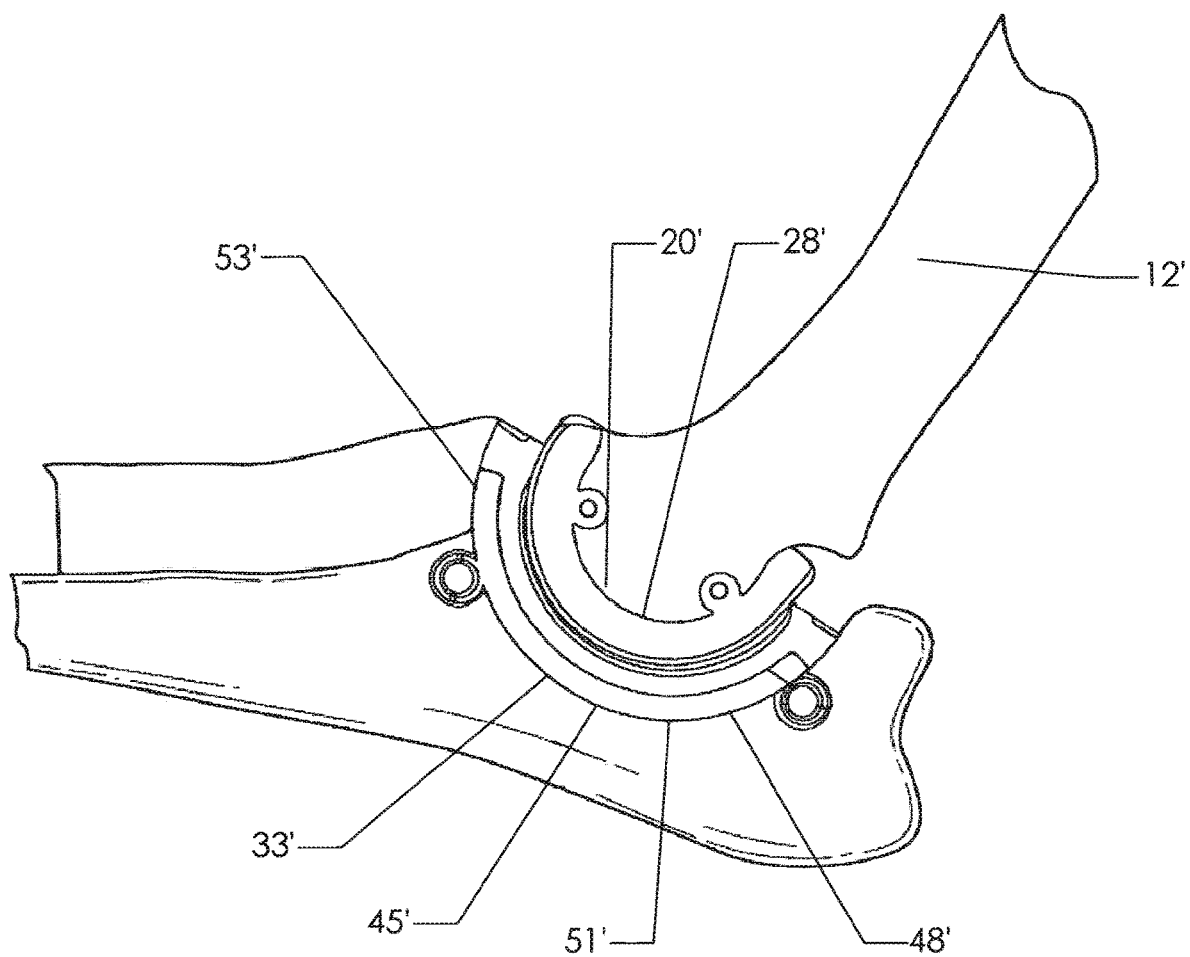
FIG. 2 is a side view of the implant of FIG. 1 including the humerus, radius and ulna.
Figure 13:
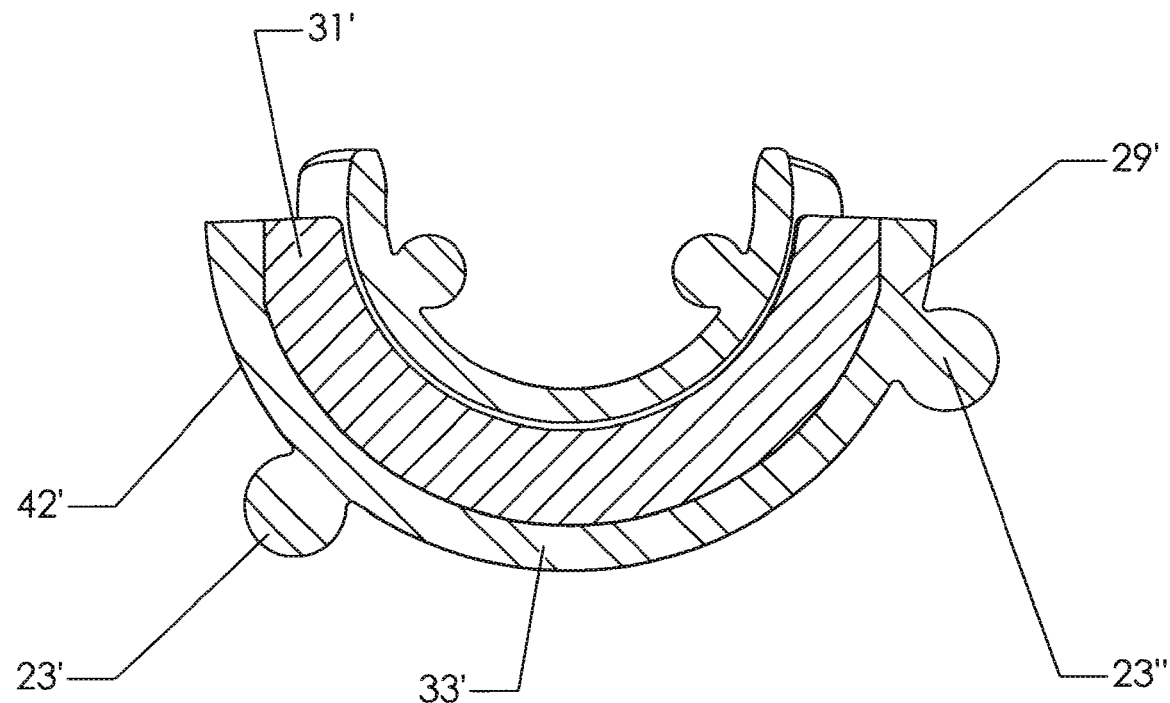
FIG. 13 is a cross-sectional view about lines 13-13 of the implant shown in FIG. 11.
Figure 14:
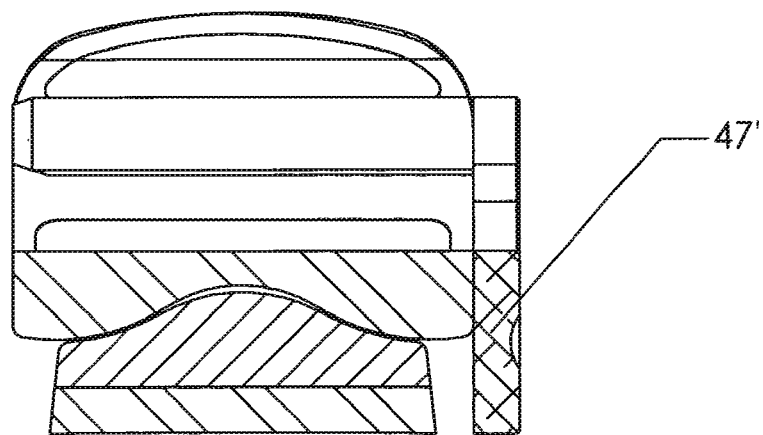
FIG. 14 is a cross-sectional view about lines 14-14 of the implant shown in FIG. 7.

As shown in FIG. 2, the second articulating surface portion 31' of the radioulnar component 29' slides or pivots about a major axis (i.e. the central axis of rotation of the joint) in relation to the first articulating surface portion of the humeral component 13', forming an articulating system. The radioulnar component 29' as shown in FIGS. 3, 11 and 13 is made of two pieces, namely, the second articulating surface portion 31' and the second bone fixation portion 33'. The second articulating surface portion 31' is made of ultra-high molecular weight polyethylene but may also be made of other materials such as PEEK and PEKK. The second bone fixation portion 33' may be composed of cast cobalt chrome molybdenum, titanium or ceramic, or porous tantalum as well as other materials. This allows the articulating surfaces of the humeral and radioulnar components 17' and 31' to have metal-on-plastic contact. Other combinations may be used without departing from the intent of providing a smooth, articulating surface.

Figure 5:
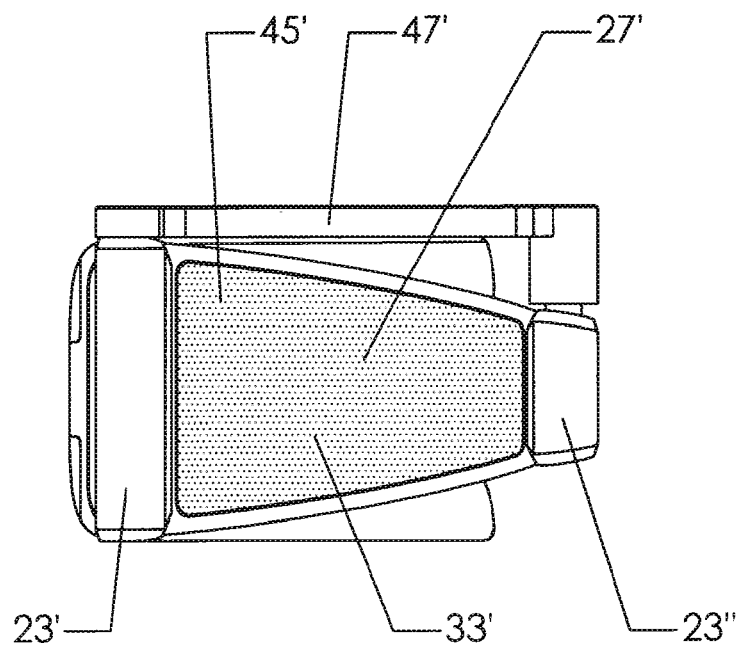
FIG. 5 is a bottom plan view of the implant as shown in FIG. 1.
Figure 6:
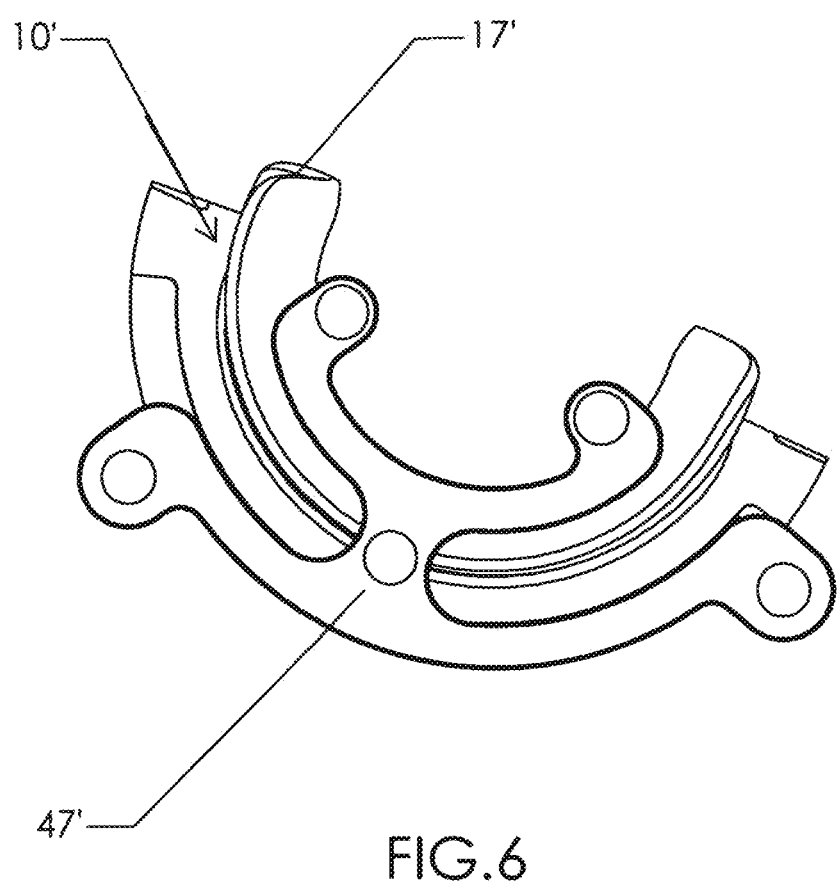
FIG. 6 is a side view of the implant of FIG. 1 including the set plate.
Figure 7:
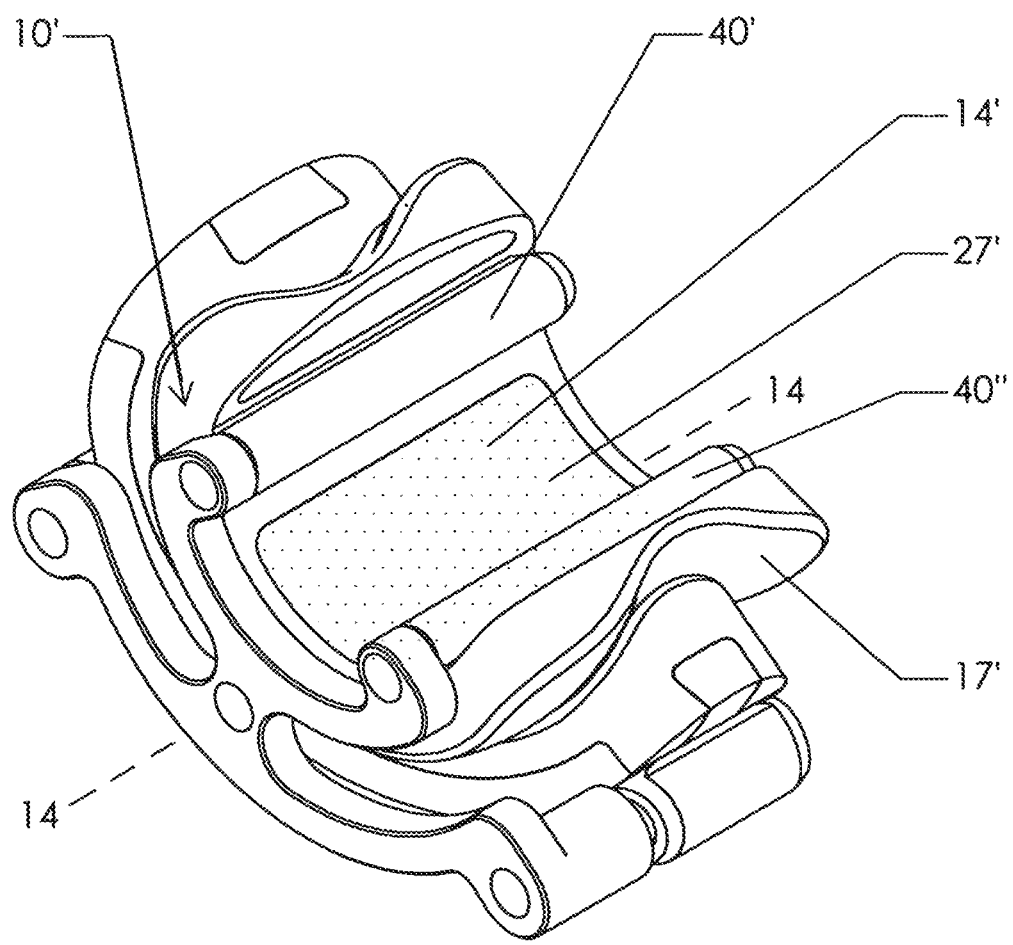
FIG. 7 is a perspective view of the implant shown in FIG. 1.
Figure 8:
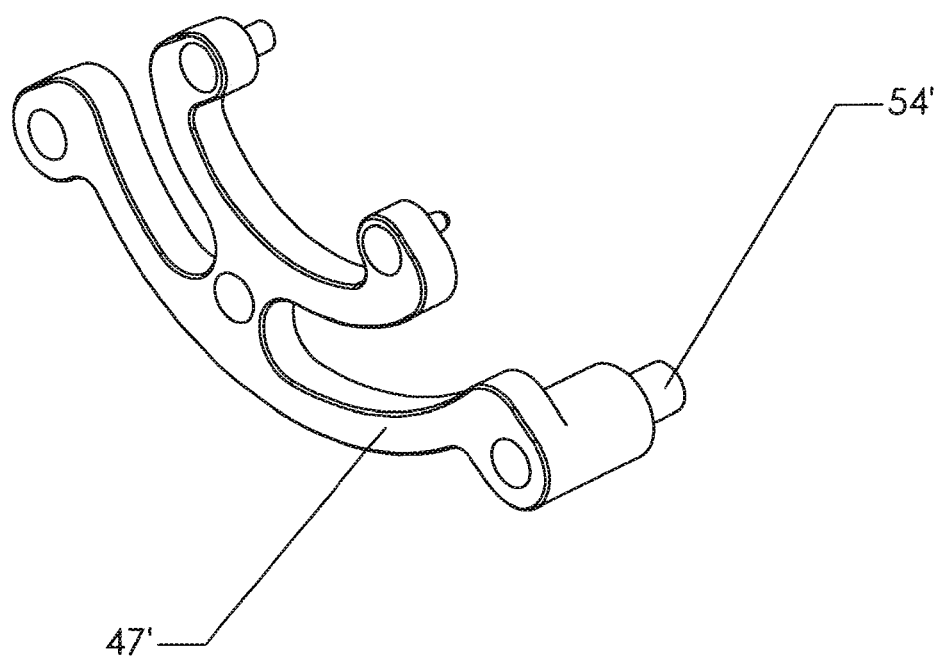
FIG. 8 is a perspective view of a set plate.

The second bone fixation portion 33' of the radioulnar member 29' contains at least one retaining member 23', but in the case at hand has two retaining members 23', 23", with hollow openings 22', 22" to aid in implant positioning. As with the transversely extending retaining members 40', 40" of the humeral component 13', the retaining members 23', 23" of the radioulnar component 29' also may be cylindrical and transversely extending along a major axis of the radioulnar component 29'. Further, the retaining members 23', 23" in this embodiment as shown in FIGS. 11 and 13 do not extend beyond an outer peripheral edge 42' of the second articulating surface portion 31' of the radioulnar component 29'. This is by way of example, but the retaining members may also extend beyond the outer peripheral edges of the radioulnar component or end short of the outer peripheral edges as well. As with the humeral component 13', the second bone fixation portion 33' of the radioulnar component 29' may also integrate porous beads 27' to promote bone ingrowth as shown in FIGS. 4 and 5. A distal portion 45' of the radioulnar component 29' which is the second bone fixation portion 33', contacts proximal surfaces of the ulna 51' and radius 53' providing for an interference fit between the second bone fixation portion 33' and the radius and ulna.

In one embodiment, the groove 15' and ridge member 37' are not centered but the complementary components are longitudinally extending and intersect a major axis only at the center as discussed previously, requiring a different joint prosthesis for the right and left joints. It will be evident that in another embodiment, the prosthesis, including humeral and radioulnar components, is isometric, and can be used for a right or left joint arthroplasty with the complementary components extending longitudinally along a centered vertical plane.

The articulating surfaces of the humeral and radioulnar components are polished to a smooth finish promoting unencumbered articulation between the two surfaces. The bone fixation portions of the humeral and radioulnar components contain the retaining members 23', 23" and 40', 40" on their surfaces to provide initial stabilization to promote bone ingrowth. The humeral and radioulnar components 13' and 29', typically have a specific thickness when combined of 8 mm, however this could range from 2 mm to 40 mm depending upon the size of the joint. The humeral and radioulnar components are releasably linked together with an aligning or retaining piece or set plate 47' as shown in FIGS. 8 and 12A-12D that aids in positioning of the implant 10' [11'] within the joint cavity 48', as shown in FIG. 2, and is removed once the implant is securely in place. The combination of the implant 11' and the set plate 47' forms an aggregate joint prosthesis 10'. The implant set plate 47', for example, has at least two arms extending outwardly and in this embodiment has four arms extending outwardly. The set plate 47' is inserted simultaneously with the components into the joint cavity, to be discussed in greater detail, and serves multiple functions; due to the complexity of articular surfaces of a mammal in general, it is necessary that when placed in the subject, both components be oriented at the proper depth and in the proper state of articulation as is defined by the surgical procedure and specifically the drilling and milling process, as well as guaranteeing proper alignment between articular surfaces of both components, in this case the humeral component 13' and the radioulnar component 29', eliminating the possibility of joint compartment loading with misaligned implants primarily caused by surgical errors in surface preparation and implant insertion. The set plate 47' provides a one-step method of joint insertion, reducing surgical error and guesswork while minimizing trauma to the subject joint. Prior art prosthetics in general may fail based on improper loading of the joint surfaces due to misalignment of multi-component prosthetics. Typically, a joint prosthesis is implanted using multiple steps including for example, implantation of a humeral component followed by implantation of a radioulnar component in a canine. For example but not by way of limitation, the canine elbow is typically aligned at 90° flexion for surgical purposes, as shown in FIG. 2. The 90° flexion provides the maximum overlap of articular surfaces of the joint while allowing for the minimum amount of joint preparation for all pertinent surfaces simultaneously. The implants, to function correctly together, should both be at their respective 90° of flexion and inserted to a proper depth.

The set plate 47' has four end members 57', 59', 61' and 63', as shown in FIG. 12D, including posts of variable size and shape 49', 50', 52' and 54' that releasably link the humeral component 13' and the radioulnar component 29', as shown in FIGS. 1, 4, 6, 7, and 13. The set plate 47' may be made of cobalt chrome or plastic and the posterior ulnar post 54' on the retainer 47' is slightly larger which compensates for the tapering in the posterior end 30' of the radioulnar component 29' and assures that the implants cannot go in crooked or at an angle to the sagittal plane that exists at the elbow at the point of intersection between the center line of the humerus and the center line of the radioulnar component. The retainer 47' also provides a surface for impaction of the implant upon which one can hammer or press to assure maximum insertion of the aggregate implant 10' into the joint cavity. The retainer 47' is then removed from the joint cavity while the implant 11' remains securely within the joint cavity. Due to the nature of the implant, the radioulnar component 29' relies heavily upon the press-fit nature of the component to insure stability. The humeral component 13' is captured between the medial and lateral epicondyles preventing movement laterally on a frontal or transverse plane.

As embodied and broadly described herein, the elbow arthroplasty of the present embodiment includes a humeral component 13' and a complementary radioulnar component 29' as well as the set plate 47'. The aggregate prosthesis 10' is implanted in one stage as opposed to separate stages as previously conducted in the prior art.

The implant 11' is lined up with the implant retaining plate 47' in place, all four post members 49', 50', 52' and 54' lining up with the four horizontal retaining members 40', 40'", and 23', 23" located on the first bone fixation portion 14' of the humeral component 13' and the second bone fixation portion 33' of the radioulnar component 29'. This allows the aggregate implant 10' to be inserted where the articulating surfaces have been removed. Using a hammer or press device, not shown, the aggregate implant 10' will be tapped or pressed into place within the joint cavity. The press-fit nature of the implant allows for primary fixation of the prosthesis. With the transverse retaining members, the implant may not rotate on a sagittal plane while inside the elbow. The transverse retaining members also prevent the implant from sliding side to side based on a press-fit of the joint and stabilize the implant so that bony ingrowth into porous surfaces may occur, which is the secondary fixation that occurs.

The aggregate implant 10' is placed above the cavity created by the drilling and milling process, to be discussed at a later point, and is impacted or pressed into the cavity until it reaches the proper and pre-defined depth. As a result of the accuracy and reproducibility of the drilling and milling process, there is almost no distance between the aggregate implant 10' and the bone. Optimally, the implant is set within 1 mm of the bone. If there is more than 1 mm. of space between the implant 11' and the bone, there is increased potential for poor bone ingrowth. Cementless fixation is utilized in our method but is set forth as an example, not as a limitation. Once the aggregate implant 10' is in place, the set plate 47' is removed manually. The medial condylar crown, including the attached ligaments and muscles, is reattached, not shown, using a 3.5 mm cancellous screw, not shown. The cancellous screw is manufactured by Veterinary Orthopedic Implant, Synthes or New Generation Device or any other manufacturer of bone screws.

Figure 15:
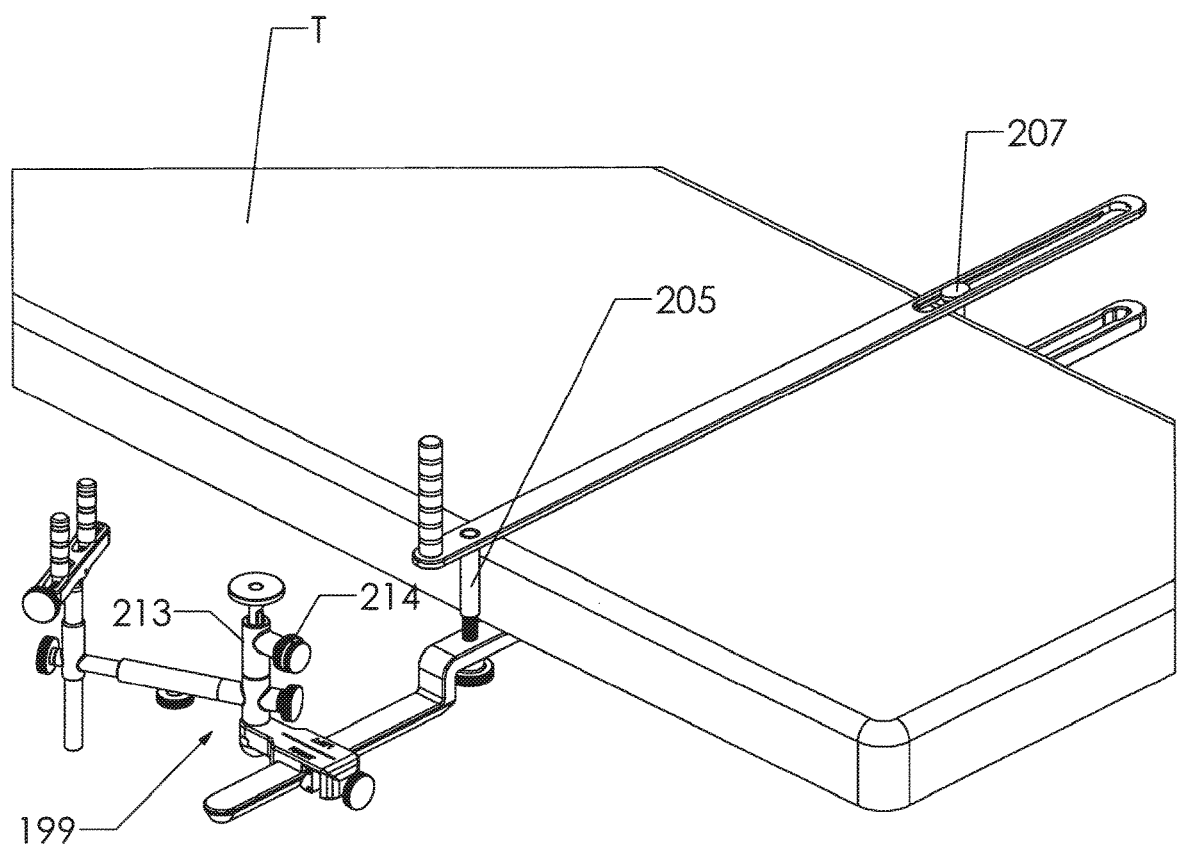
FIG. 15 is a perspective view of a positioning system.
Figure 16:
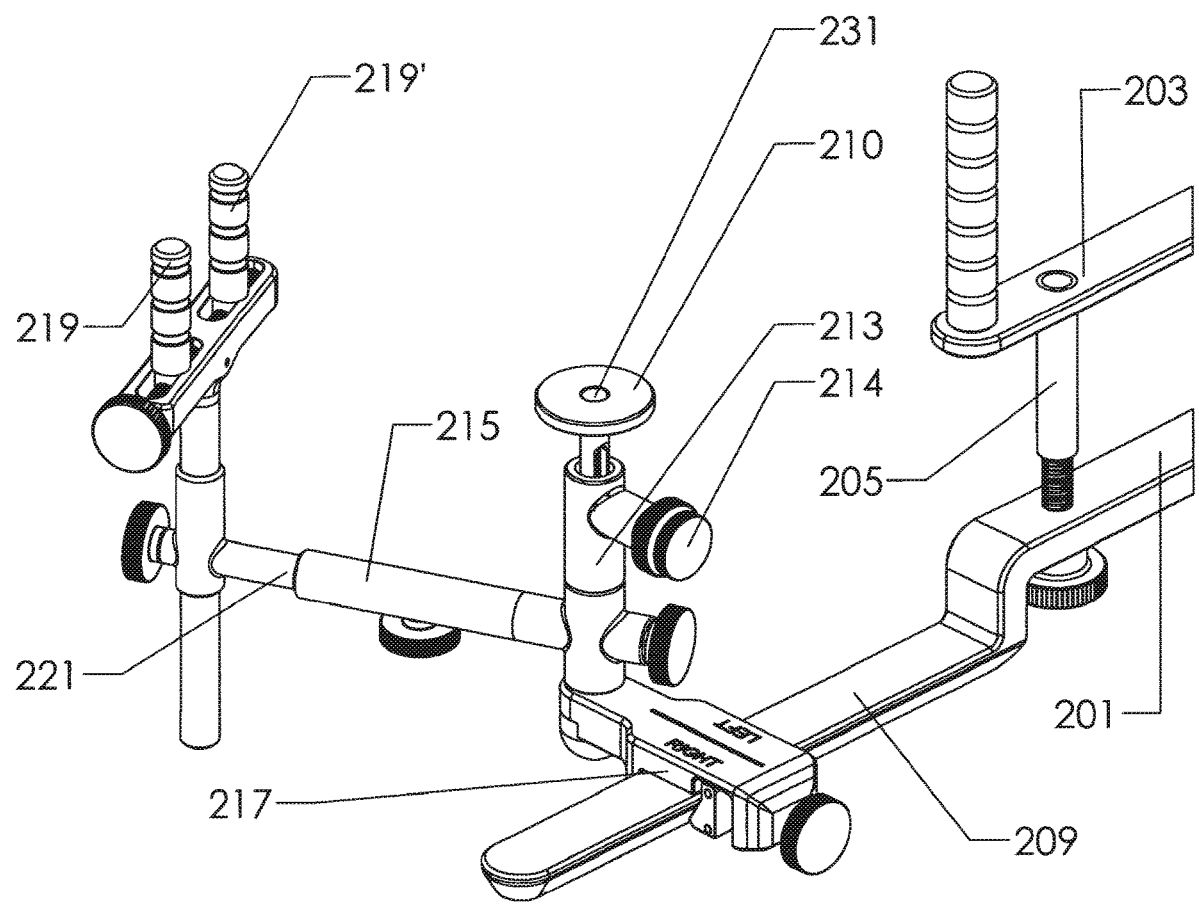
FIG. 16 is a perspective view of the positioning system shown in FIG. 15.

There is also described a novel and improved method for implantation as well as embodiments of a positioning device 199 as shown in FIGS. 15-16, an alignment plate 229 as shown in FIGS. 17-21, a drill template 259, as shown in FIGS. 22-26 and a milling guide and system, as shown in FIGS. 29-36 for the installation of the implants. Broadly, a medial or lateral epicondyle or malleolus osteotomy is performed, the central axis of rotation of the subject joint is established, the subject limb is stabilized in a positioning device, drilling and milling are completed on the subject joint, the aggregate prosthesis is implanted into the joint cavity, the set plate 47' is removed and the medial epicondyle is reattached.

The implant 11', instruments and method are useful in the treatment of degenerative joint disease in mammals and allow for a minimally invasive implantation technique. The joint is not luxated during the process and the ligaments and muscles remain attached to the bony structure. The aggregate prosthesis is implanted in one stage as opposed to separate stage procedures. Prior art involves securing a multi-piece implant in consecutive steps to the opposing or complementary bone structures, for example with the elbow, the humerus, radius and ulna.

In one method, offered by way of example only, a radiographic evaluation including radiographs as well as arthroscopic surgery are performed on the subject to determine the degree of disease and to measure and estimate the proper size of implant to be used in the procedure. A template or digital overlay, not shown, is also used to determine the size of the implant necessary. The subject joint is prepared and a medial joint is exposed for osteotomy. An osteotomy guide (not shown) is clamped to the medial condyle of the subject. The osteotomy guide is a hemostat-like instrument that uses specific anatomical references to perform an accurate resection of the medial epicondyle. A saw blade, not shown, is inserted through a cutting slot and accurately cuts the bone. Once the medial epicondyle has been osteotomized, not shown, the cut portion which is the condylar crown is reflected back along with the attached flexor muscles and medial collateral ligaments, exposing the distal medial humeral condyle.

The next step involves locating the central axis of rotation of the subject joint. Using a guide, a 2.5 mm "C.O.R." (Center of Rotation) bore is drilled through the central axis of rotation of the joint using a hand drill and a specifically designed instrument, not shown, that aids in location of the central axis of rotation of a hinge joint. The COR bore functions as a reference for every surgical step thereafter and aids in proper positioning of the implant as well as positioning of the alignment plate 229, drill template 259 and milling arm 301. In this instance a drill is used to drill through the central axis of rotation. Once the COR bore is drilled, a CORpin 70 is inserted medially up to the flange 73 which leaves an extended portion, the upper post 71, extending out of the medial side for attaching various instruments such as, but not limited to, the alignment plate, drill guide and milling arm. The COR pin 70 extends through the joint and out the lateral side where it is inserted into a COR base 213 on the positioning device 199 and locked into position with a thumb screw 214 located along the COR base 213. Broadly, the positioning device 199 as shown in FIGS. 15 and 16 stabilizes and supports the joint for ease of operation. The positioning device 199 consists of a base arm 201 that runs parallel to an upper arm 203, both secured respectively in parallel by adjustment members 205 and 207. The base arm 201 and upper arm 203 are secured to a table T as shown in FIG. 15. A lower support member 209 extends from the lower base arm 201 providing support for the COR base 213. The COR base 213 has a circular platform support 210 that includes a COR post opening 231 and an adjustable arm 215 extending transversely of the COR base 213, the arm 215 having spaced upstanding dual post members 219,219' that are provided for limb support. The lower support member 209 is adjustable with linear clamp 217 to accommodate a variety of subject sizes, and the arm 215 is also adjustable by utilizing a telescoping adjustment member 221. Once the COR pin 70 is inserted into COR post recess 231 and secured into place, the subject limb and joint are positioned in proper alignment for the next surgical steps.

Figure 17:
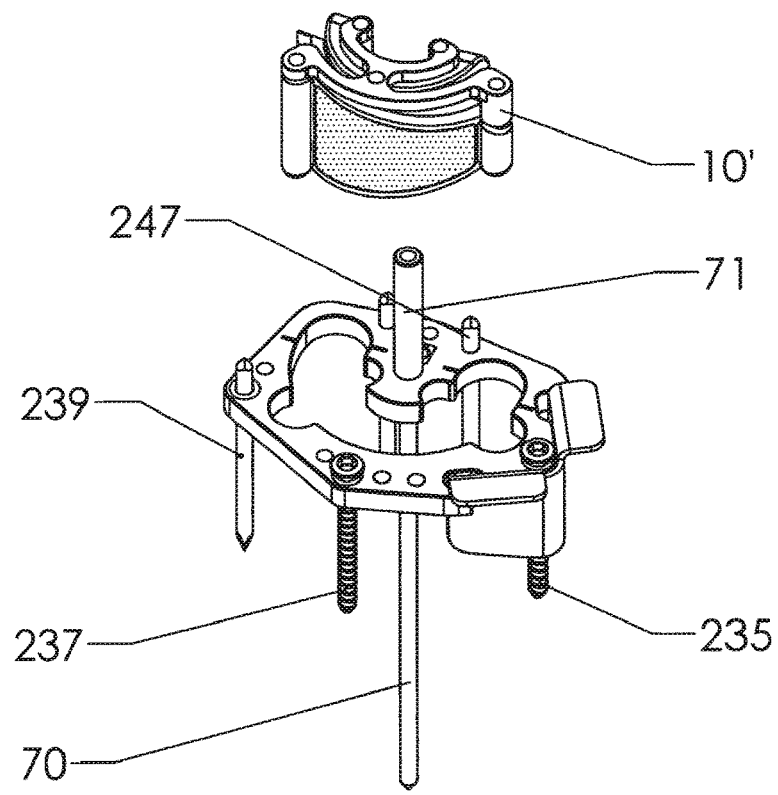
FIG. 17 is an exploded perspective view of an alignment plate, a center of rotation post and an aggregate prosthesis.
Figure 18:
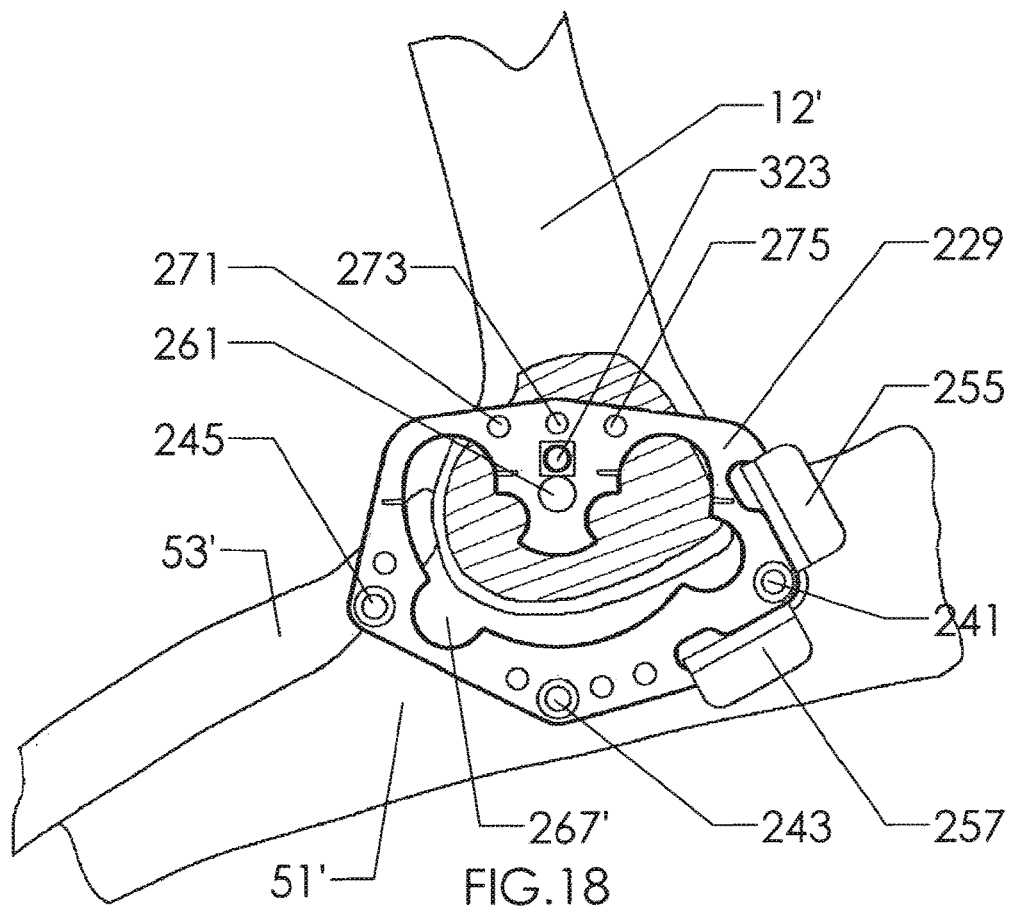
FIG. 18 is a top plan view of the assembly of the alignment plate of FIG. 17 including the humerus, radius and ulna.
Figure 22:
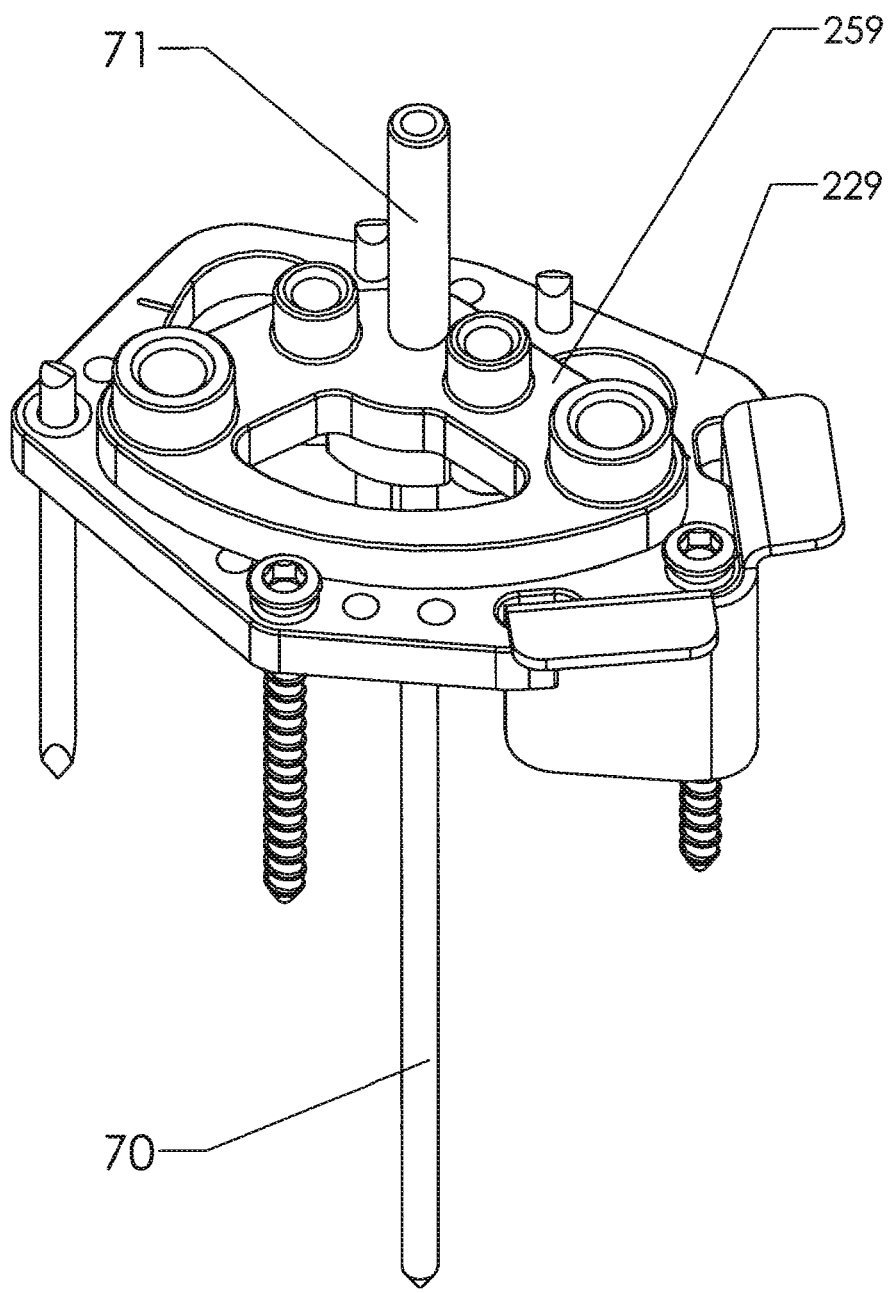
FIG. 22 is a perspective view of an alignment plate, center of rotation post and drill guide.
Figure 26:
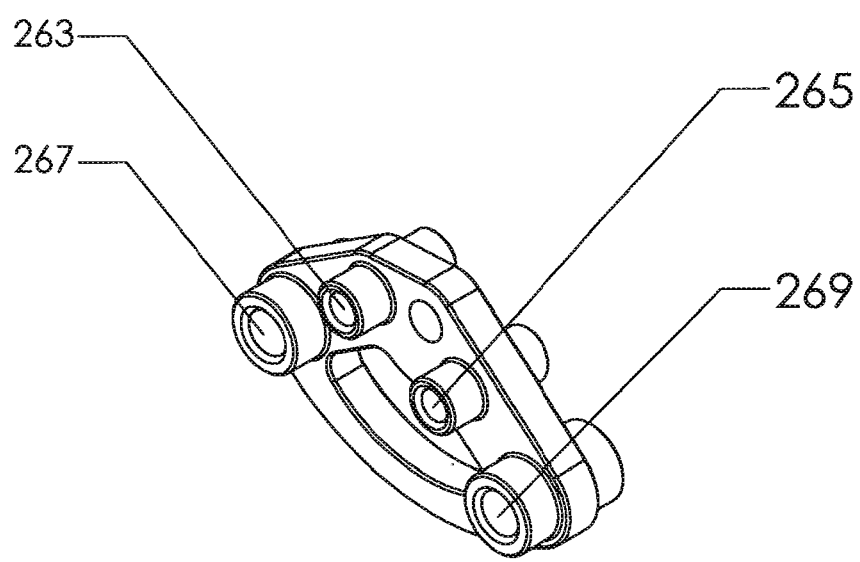
FIG. 26 is a perspective view of a drill guide.
Figure 27:
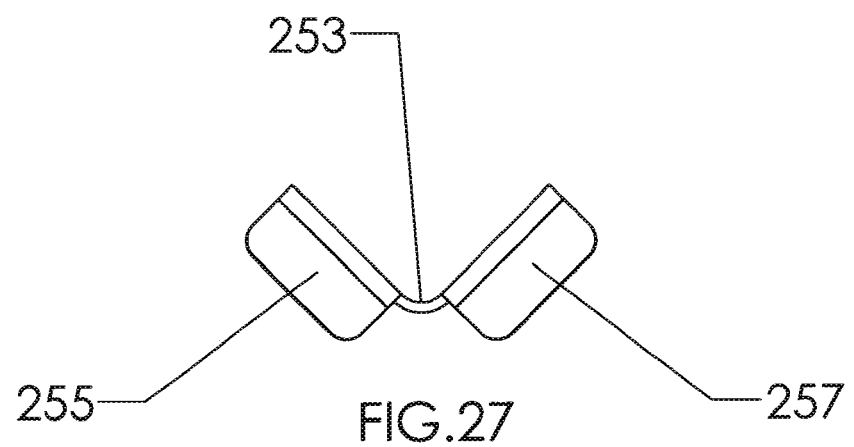
FIG. 27 is a top plan view of a retraction plate shown in FIG. 22.
Figure 28:
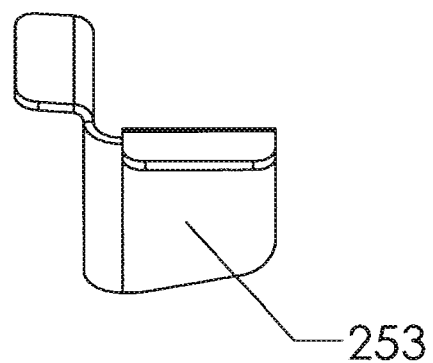
FIG. 28 is a perspective view of a retraction plate.

For example, a limb may be placed between and cradled with dual post members 219, 219', exposing a medial or lateral joint for placement of the COR post 70 through the COR bore in the joint from a medial to lateral aspect and locked into place within the COR base 213 with the thumb screw 214. Once the COR pin 70 is locked in place, the alignment plate 229 slides over the COR post 71 via opening 261 as shown in FIGS. 17 and 18. The alignment plate 229 broadly is of pentagonal configuration with level upper and lower surfaces as shown in FIGS. 19 and 21. The plate 229 is of uniform width with the exception of a centrally located cut-away portion or milling window 230 approximating the cross-sectional configuration of the aggregate prosthesis 10' at approximately 90° of articulation as shown in FIG. 20. The milling window 230 is defined by lateral edges 234 surrounding the window 230. The configuration of the alignment plate 229 and therefore the milling window 230 will vary depending upon the articulation surface to be resected and the configuration of the prosthesis to be inserted. Upon mounting the alignment plate 229 over the COR post 71, the plate 229 is rotated until the cranial edge of the milling window 230 aligns with the cranial osteochondral junction of the humerus. A Steinmann pin or k-wire, 247, shown in FIG. 17, is inserted through openings 271,273 or 275 in the alignment plate 229 and into the distal end of the proximal bone, in this case the humerus. The joint is then brought into a degree of flexion, and the cranial peg portion 267' that is part of the milling window 230 aligns with the middle of the radius 51' at which point cancellous bone screws 235,237, and 239 are inserted through respective holes 241,243 and 245 in the alignment plate and into bone, superimposing the plate onto the side of the joint, and locking the plate in the desired position. A second or third k-wire, Steinmann pin, or bone screw may be placed through openings 271,273 or 275 to increase the stability of the joint. Optionally, a posterior retraction plate 253, as shown in FIGS. 27 and 28, may be used with posterior tabs 255 and 257 aiding in retraction of ulnar nerves and soft tissue from encroaching on the drilling and milling processes. Shoulder edge supports 254 and 256, as shown in FIG. 20, are present on the alignment plate to provide a means for locking the retraction plate 253 in position. Once the alignment plate 229 is secured to the surface of the medial condyle, a drill guide template 259 is then placed over the COR post 71, through opening 261 and superimposed on the alignment plate 229, as shown in FIGS. 22 and 26.

Figure 24:
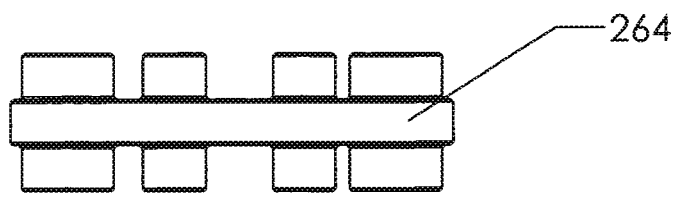
FIG. 24 is a side view of a drill guide.
Figure 25:
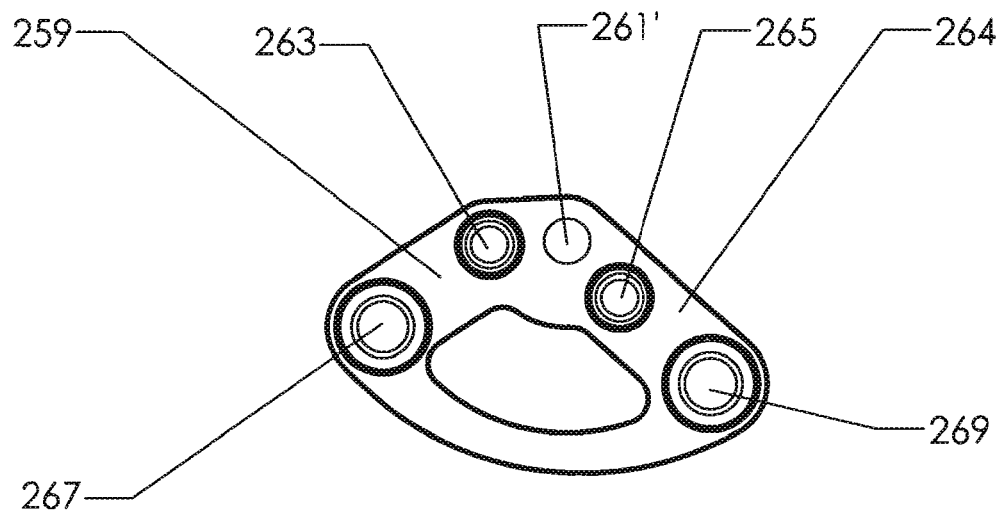
FIG. 25 is a bottom view of a drill guide.

The drill template 259 is slightly smaller in overall size than the alignment plate 229. The drill template is of substantially triangular configuration having protruding annular bosses extending upwardly and downwardly from a base 264 of the drill template as shown in FIG. 24. The template has two annular bosses 263 and 265 that are either 2.7 mm or 3.2 mm in diameter and two additional annular bosses 267 and 269 that are either 3.2 mm or 4.5 mm in diameter depending upon the size of the joint. The radial distance of the annular bosses 263, 265, 267 and 269 changes with the size of the joint and are designed to allow for a 2.7 mm, 3.2 mm, or 4.5 mm drill bit to pass through. Bore 261' of the drill template slides over the COR post 71 and the annular bosses 263,265,267 and 269 align over the appropriate and corresponding openings 263', 265', 267' and 269' in the milling window 230 of the alignment plate 229. In use, the drill template 259 is superimposed on the alignment plate 229 and the four protruding annular bosses 263,265,267, and 269 correspond to the cranial and caudal peg bores 263', 265', 267' and 269' on the alignment plate and correspond as well to the humeral implant retaining members 40', 40" and the radioulnar implant retaining members 23', 23". Once the drill template is attached and properly positioned using the COR post as a reference for the central axis of rotation, drill bits are inserted through the four annular bosses in order to form a portion of the recess for the joint prosthesis. The drill template 259 is then removed and the milling process is started.

Figure 23:
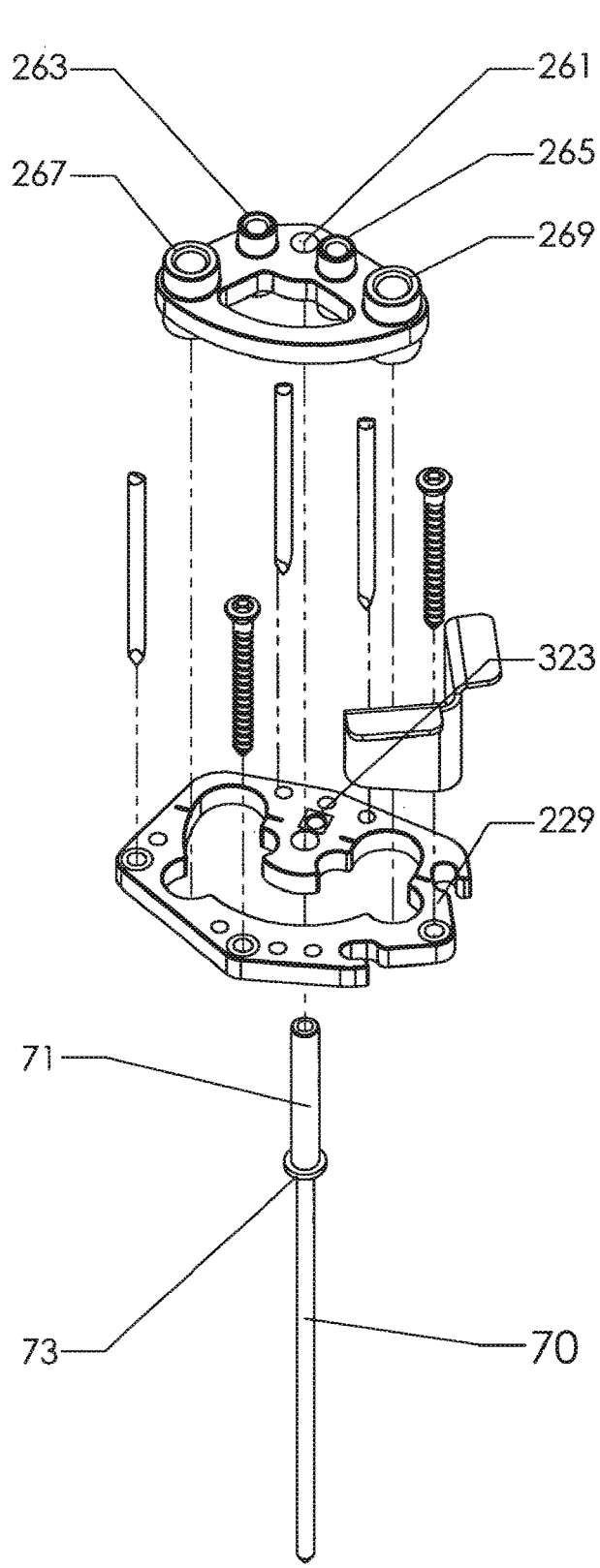
FIG. 23 is an exploded view of an alignment plate, center of rotation post and a drill guide.
Figure 29:
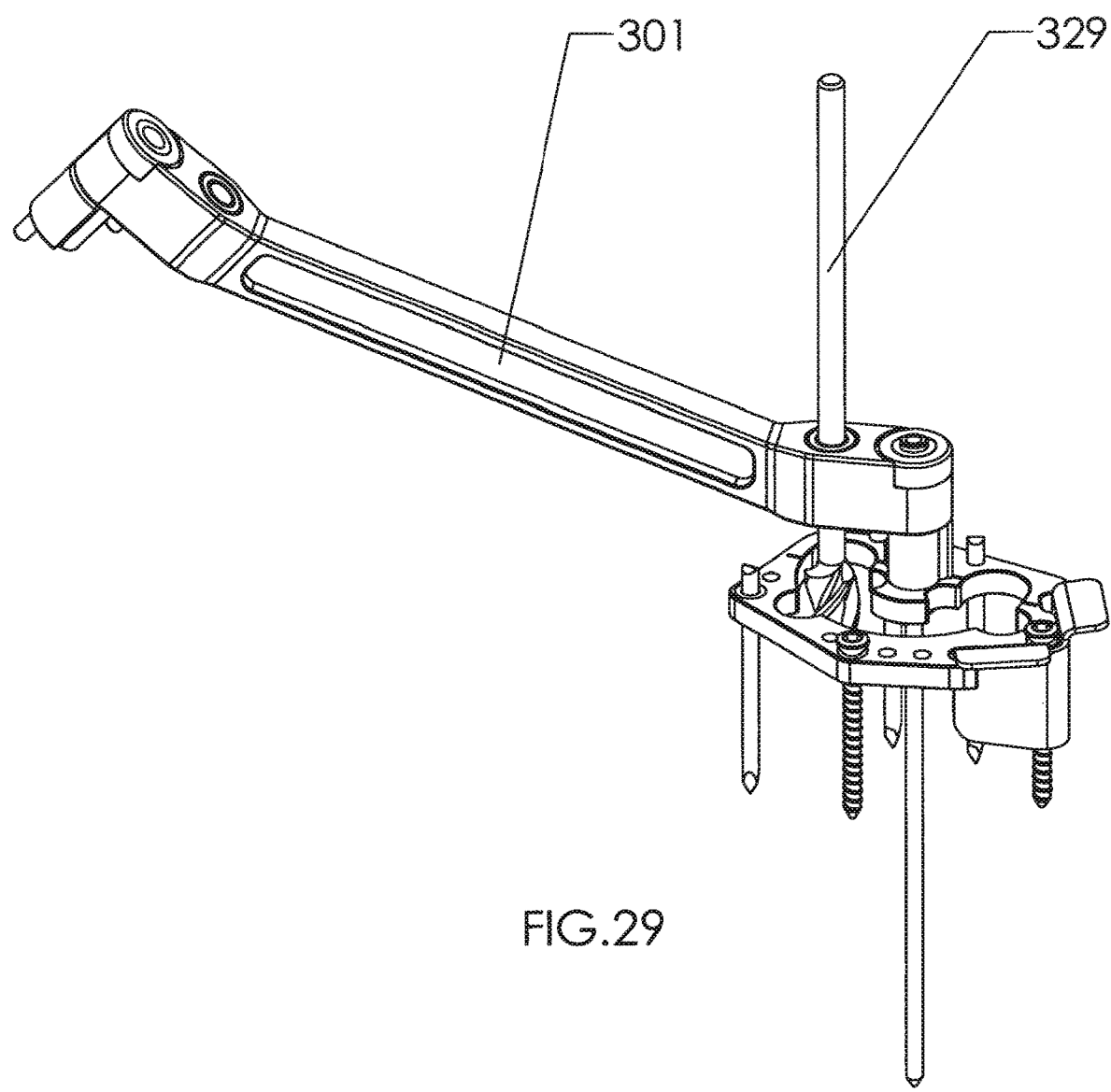
FIG. 29 is a perspective view of a milling arm, alignment plate and center of rotation post.
Figure 30:
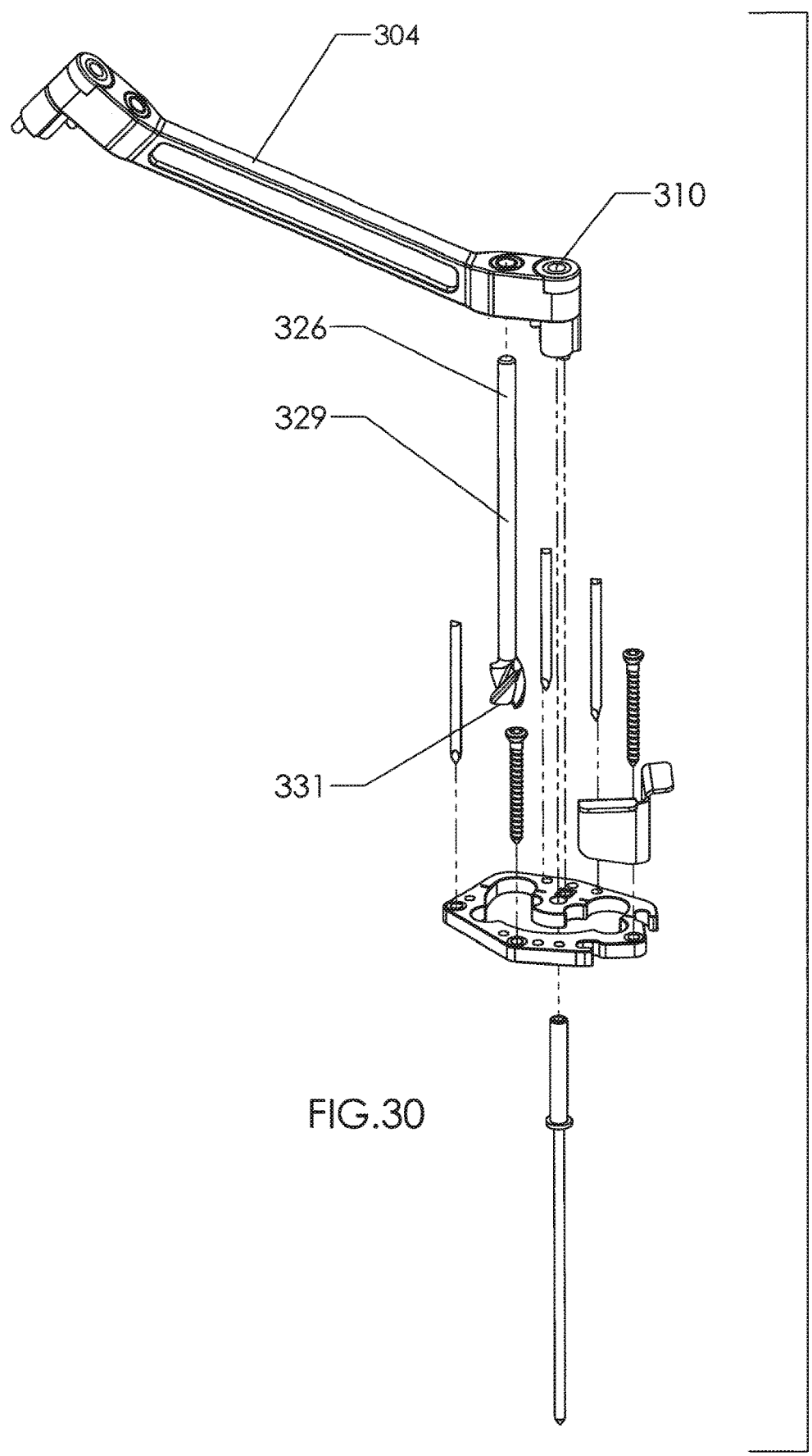
FIG. 30 is an exploded view of a milling arm, an alignment guide and a center of rotation post.
Figure 31:
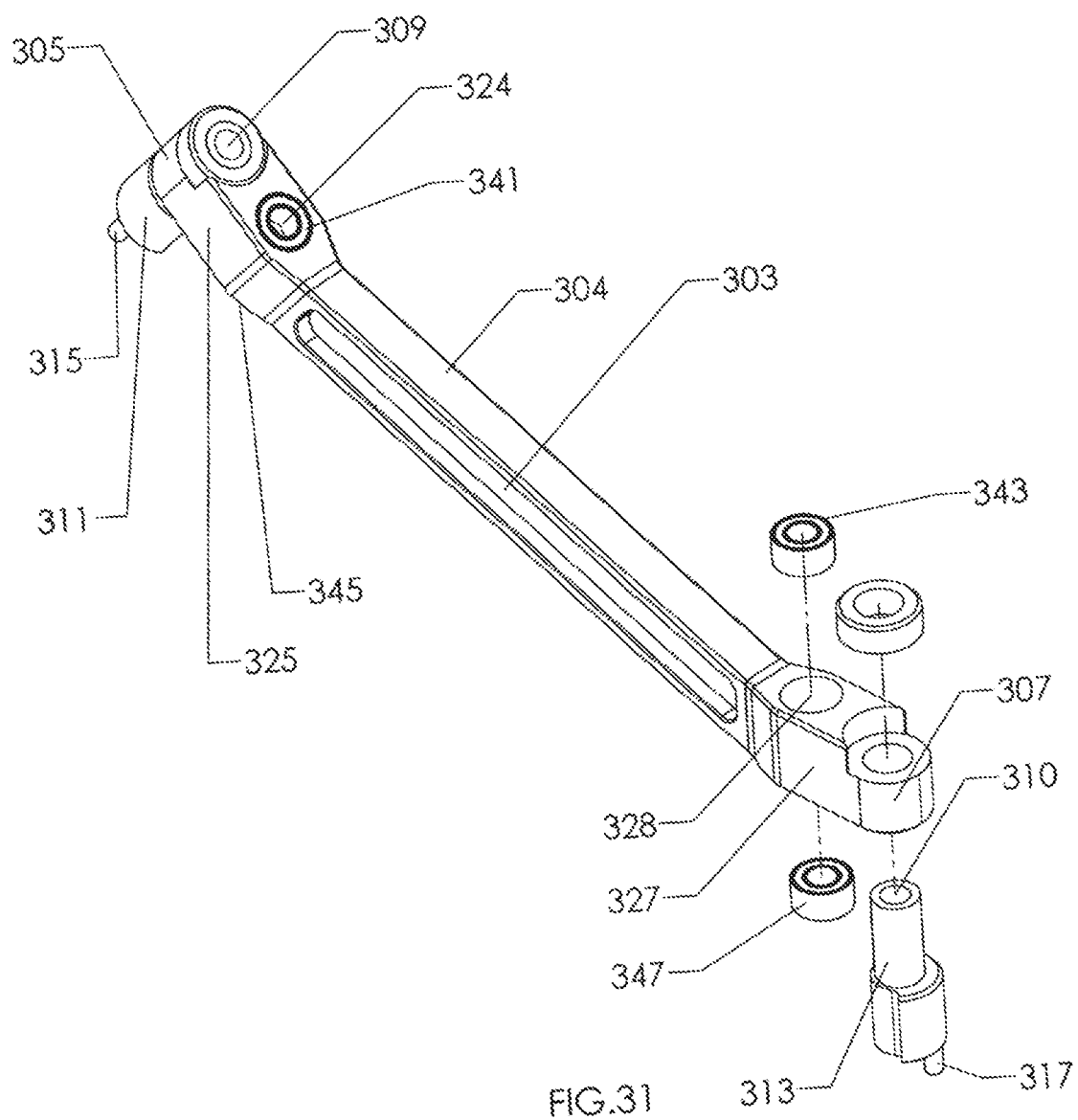
FIG. 31 is a perspective, exploded view of a milling arm.
Figure 32:
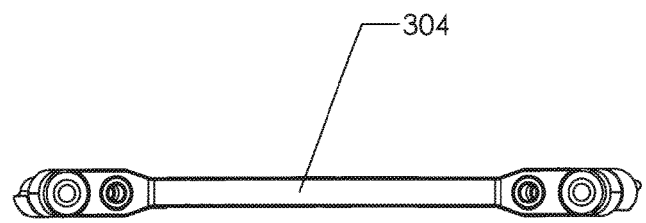
FIG. 32 is a top plan view of a milling arm.
Figures 33, 35, 36:
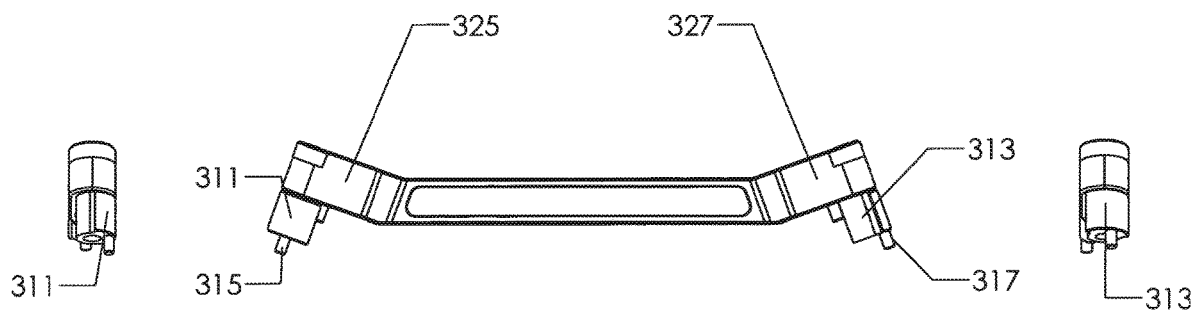
FIG. 33 is a side view of the milling arm of FIG. 30.
FIG. 35 is a perspective view of an end of the milling arm of FIG. 30.
FIG. 36 is a perspective view of a second end of the milling arm of FIG. 30.
Figure 34:
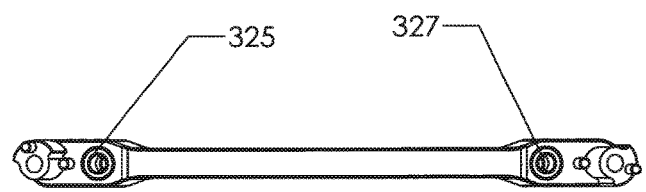
FIG. 34 is a bottom view of the milling arm of FIG. 30.

A specially designed milling apparatus 301 shown in FIGS. 29-36 is utilized to accurately and reproducibly resect a joint and more specifically to remove articular surfaces and prepare the joint cavity for insertion of the aggregate prosthesis. The milling system accurately removes remaining cartilage and minimal subcondylar bone while preserving good trabecular structure. Subsidence typically occurs when the compressive stresses exceed the strength of the bone, resulting in microfractures and resorption of trabeculae. Resurfacing of the articular surfaces of the humerus, the radius and ulna of the canine elbow, for example, is performed with the milling arm 301 and custom end mill 329. The milling arm 301 is adaptable to accommodate various types of instruments to aid in milling, for example, to prepare the joint for insertion of the prosthesis and comprises a milling shaft 304, as shown in FIG. 30, that is designed to be placed over the COR post 71 for stabilization and orientation. The milling arm 301 may take a number of forms but by way of example is shown in FIGS. 32 through 36 as having a linear shaft portion 304 with upwardly extending end mounts 325 and 327 as well as adaptors 311 and 313 journaled at opposite ends. Each adaptor is roughly at an acute angle to the shaft 304 and extends downwardly from the end mounts 325 and 327. Each of the end mounts 325 and 327 are designed to mill a size specific mill path to accommodate different sized implants. The adaptors 311 and 313 include sized pin fittings 315 and 317 for extension into the alignment plate 229. The opposite end adaptors 311 and 313 allow the milling apparatus to be adaptable for use with different sizes of implants. For example but not by way of limitation, once the COR post 71 is inserted in bore 309 or 310, one of the adaptor fittings 315 or 317 is inserted into the bore 323 in the alignment plate 229, as shown in FIG. 23. The placement of adaptor fitting 315 or 317 into the bore 323 in the alignment plate 229, allows the milling arm 301 to rotate a pre-determined amount in an arc-shaped configuration for accurate removal of designated joint surfaces via the end mill for placement of the prosthesis The opposing ends 305 and 307 of the milling arm 301 are utilized depending upon the size of prosthesis required for implantation. Each size of prosthesis requires a corresponding alignment plate to assure proper and accurate removal of joint surfaces.

The custom bone end mill 329 is inserted through entry port 324 or 328 and inserted into a rotary handpiece while mill end member 331 passes through the milling window 230 of the alignment plate 229 thereby allowing the end mill 329 to pivot, in a controlled fashion, with the milling arm 301 in a radial arc around the center of rotation (i.e. the COR Post) and simultaneously resurface the joint surfaces for implantation of the aggregate prosthesis. A depth measuring device or depth limiting stop, not shown, is used to ensure proper depth penetration. The mill end member 331 moves through the large arc-shaped milling window 232 within the alignment plate 229, resulting in simultaneous removal of both the humeral and radioulnar articular surfaces from a medial or lateral aspect. The milling device 301 enables a user to lock the milling device over the COR post 70 and rotate the milling device horizontally through a designated arc based on the arc formed by the insertion of the adaptor fittings 315 or 317 and the bore 323 as described above. The end mill 329 is inserted through the milling arm bore 324 or 328 and is adapted to pivot around the COR, bearing members 341, 343, 347 and an additional bearing member that is not shown, allow the end mill 329 to spin at high speeds via the rotary handpiece and motor. The drilling and milling systems allow the surgeon to prepare all pertinent articular surfaces simultaneously and all surfaces reference the natural central axis of rotation of the joint. The milling window 232 in the alignment plate is configured such that when the adaptor fittings 315 or 317 are mounted on the adaptor in one of the sockets, the mill end member 331 will remove only the articular surfaces within range of the guide path and the mill end member cannot travel beyond the path configuration defined by the alignment plate as shown in FIGS. 29 and 30. Further, the adaptors and adaptor fittings may be modified as well as the configuration on the alignment plate to allow for the desired amount of joint surface removal.

An upper portion 326 of the end mill is locked in a rotary handpiece which is attached to a low speed high torque motor manufactured by Foredom Power Tools and is held in one hand while the milling arm 301 is held in the other hand and pivoted around the COR pin as the joint surfaces are milled. This results in a controlled, stable process for removing articular surfaces and allowing for accurate and easy removal of the articulating joint surfaces, virtually avoiding the potential for operator error. The milling arm bore 324 and 328 may take many forms but are designed to enable an approach that is parallel to the central axis of rotation of the joint, providing stabilization. The milling window 230 as well may take different forms and may accommodate different tools to allow for varied forms of cartilage and bone removal.

Once the surfaces are simultaneously removed, the alignment guide is left in place and the aggregate prosthesis is press-fit through the window 230 in the alignment plate and into the space removed through the milling and drilling processes.

Due to the insertion of the implant from the medial or lateral aspect, the humeral and radioulnar articulating surfaces may be resurfaced without having to luxate or otherwise open or expose the articulating surfaces of the joint which could result in unwanted damage to the surrounding soft tissue. The removal of articular cartilage as well as a minimal amount of subcondylar bone on both sides of the joint simultaneously without having to disarticulate the joint allows for a minimally invasive procedure.

Referring to FIGS. 2 and 18, the implant 11' is lined up with the implant retaining plate 47' in place, all four bores lining up with the four horizontal members 40', 40", 23', 23" located on the first bone fixation portion 14' of the humeral component 13' and the second bone fixation portion 33' of the radioulnar component 29'. This allows the aggregate implant 10' to be inserted where the articulating surfaces have been removed. Using a hammer or press device, not shown, the implant 10' will be tapped or pressed into place within the elbow joint. With the members 40', 40", 23', 23" running horizontally, the implant may not rotate on a sagittal plane while inside the elbow. The horizontal members also prevent the implant from sliding side to side based on a press-fit of the joint.

In the case of a canine elbow joint, the implant retaining members 40', 40", 23', 23" are aligned with the four drill bores and are impacted or pounded into the joint cavity so that there is almost no distance between the implant and the bone. Primary fixation occurs due to the press-fit nature of the implant as a result of the retaining members, providing initial stabilization for bone ingrowth. Secondary fixation occurs as a result of the porous members allowing for bony ingrowth between the implant and the existing bony structures. Cementless fixation is utilized in our method but is set forth as an example, not as a limitation. Once the implant is in place, the implant retaining plate 47' is removed and the medial epicondylar crown, including the attached ligaments and muscles, is reattached, not shown, using a 3.5 mm cancellous screw, not shown. The cancellous screw is manufactured by Veterinary Orthopedic Implant, Synthes or New Generation Devices.

While a number of exemplary aspects, embodiments and methods have been discussed above, those of skill in the art will recognize certain modifications, permutations, additions and subcombinations thereof. It is therefore intended that the following appended claims and claims hereafter introduced are interpreted to include all such modifications, permutations, additions and sub-combinations as are within their true spirit and scope.

We claim:

1. A joint prosthesis system comprising:
    an implant;
    an alignment guide comprising:
        a post member extending through a central axis of rotation in the implant; and
        a milling guide member having first limiting member for limiting articular surface removal from a joint, the first limiting member including a recessed guide for positioning the implant.

2. The joint prosthesis system of claim 1, further comprising a second limiting member, the second limiting member including a drill guide member removably positioned on the post member.

3. The joint prosthesis system of claim 1, wherein the post member includes a retraction member.

4. The joint prosthesis system of claim 1, wherein the post member includes means for removing articular surfaces from the joint.

5. The joint prosthesis system of claim 1, wherein the alignment guide comprises a base member with level upper and lower surfaces, a centrally-located recess portion, and a center of rotation post receiving member.

6. The joint prosthesis system of claim 5, wherein the base member has a substantially pentagonal configuration.

7. The joint prosthesis system of claim 5, wherein the recess portion is adapted to receive an aggregate prosthesis therein.

8. The joint prosthesis system of claim 5, wherein the base member further includes a posterior retraction plate.

9. The joint prosthesis system of claim 8, wherein the base member includes a shoulder edge support member for locking the posterior retraction plate in position.

10. The joint prosthesis system of claim 5, wherein the drill guide member comprising a substantially triangular shaped base member having protruding annular bosses extending upwardly and downwardly from the base member and a center of rotation post receiving bore.

11. The joint prosthesis system of claim 10, wherein the annular bosses are sized to accommodate a cutting tool therethrough.

12. The joint prosthesis system of claim 11, wherein the annular bosses correspond to cranial and caudal retaining members on an aggregate prosthesis.

* * * * *